US006262065B1

(12) United States Patent
Pearson et al.

(10) Patent No.: US 6,262,065 B1
(45) Date of Patent: Jul. 17, 2001

(54) SWAINSONINE DERIVATIVES AND METHODS FOR PREPARING THE SAME

(75) Inventors: William H. Pearson, Ann Arbor, MI (US); Erik J. Hembre, Palo Alto, CA (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/129,875

(22) Filed: Aug. 6, 1998

Related U.S. Application Data

(60) Provisional application No. 60/054,870, filed on Aug. 6, 1997.

(51) Int. Cl.[7] ............................ A61K 41/435; C07D 471/04
(52) U.S. Cl. .......................... 514/299; 546/183; 546/14; 546/15
(58) Field of Search .......................... 546/183; 514/299

(56) References Cited

U.S. PATENT DOCUMENTS

| 5,023,340 | 6/1991 | Fleet | 548/453 |
| 5,376,452 | 12/1994 | Hope et al. | 424/450 |
| 6,048,870 | * 4/2000 | Shah et al. | 514/299 |

FOREIGN PATENT DOCUMENTS

| 61-277685 | 12/1986 | (JP) . |
| WO 98/14446 | * 4/1998 | (WO) . |

OTHER PUBLICATIONS

Written Opinion issued on Jun. 30, 1999, in corresponding Application No. PCT/US98/15804.*
Pearson et al, *J. Org. Chem.*, vol. 57, pp. 3977–3987 (1992).
Pearson et al, *Tetrahedron Lett.*, vol. 32, pp. 5513–5516 (1991).
Pearson et al, *Tetrahedron Lett.*, vol. 34, pp. 8221–8224 (1993).
Pearson et al, *J. Org. Chem.*, vol. 61, pp. 5537–5545 (1996).
Pearson et al, *J. Org. Chem.*, vol. 61, pp. 5546–5556 (1996).
Guengerich et al, *J. Am. Chem. Soc.*, vol. 95, p. 2055–2056 (1973).
Schneider et al, *Tetrahedron*, vol. 39, pp. 29–32 (1983).
Hino et al, *J. Antibiot.*, vol. 38, pp. 926–935 (1985).
Patrick et al, *Biotechnol. Lett.*, vol. 17, pp. 433–438 (1995).
Colegate et al, *Aust. J. Chem.*, vol. 32, pp. 2257–2264 (1979).
Molyneux et al, *Science*, vol. 216, pp. 190–191 (1982).
Molyneux et al, *J. Nat. Prod.*, vol. 58, pp. 878–886 (1995).
Nishimura, in *Studies in Natural Products Chemistry*, Atta–ur–Rahman, Ed., Elsevier: Amsterdam, vol. 10, pp. 495–583 (1992).
Elbein, *Ann. Rev. Biochem.*, vol. 56, pp. 497–534 (1987).
Cenci di Bello et al, *Biochem. J.*, vol. 259, pp. 855–861 (1989).
Winchester et al, *Glycobiology*, vol. 2, pp. 199–210 (1992).
Kaushal et al, *Methods in Enzymology*, vol. 230, pp. 316–329 (1994).
Goss et al, *Clin. Cancer Res.*, vol. 1, pp. 935–944 (1995).
Das et al, *Oncol. Res.*, vol. 7, pp. 425–433 (1995).
Suami et al, Chem. Letter, pp. 513–516 (1984).
Ali et al, *J. Chem. Soc., Chem. Commun.*, pp. 447–448 (1984).
Fleet et al, *Tetrahedron Lett.*, vol. 25, pp. 1853–1856 (1984).
Yasuda et al, *Chem Lett.*, pp. 1201–1204 (1984).
Adams et al, *J. Org. Chem.*, vol. 50, pp. 420–422 (1985).
Suami et al, *Carbohydr. Res.*, vol. 136, pp. 67–75 (1985).
Setoi et al, *J. Org. Chem.*, vol. 50, pp. 3948–3950 (1985).
Ali et al, *Carbohydr. Res.*, vol. 136, 225–240 (1985).
Ikota et al, *Chem. Pharm. Bull.*, vol. 35, pp. 2140–2143 (1987).
Ikota et al, *Heterocycles*, vol. 26, p. 2369–2370 (1987).
Bashyal et al, *Tetrahedron*, vol. 43, pp. 3083–3093 (1987).
Dener et al, *J. Org. Chem.*, vol. 53, pp. 6022–6030 (1988).
Carpenter et al, *Tetrahedron Lett.*, vol. 30, pp. 7261–7264 (1989).
Bennett et al, *J. Am. Chem. Soc.*, vol. 111, pp. 2580–2582 (1989).

(List continued on next page.)

Primary Examiner—Bernard Dentz
(74) Attorney, Agent, or Firm—Oblon, Spivak, McClelland, Maier & Neustadt, P.C.

(57) ABSTRACT

Compound of the formula (I):

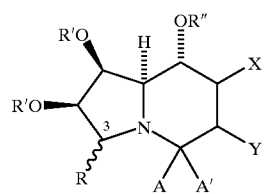

wherein:
R is defined in the specification;
each R', independently of the other, is H, acetyl, benzyl, methoxymethyl, tosyl, mesyl, trifluoromesyl, tri($C_{1-4}$ alkyl)silyl, di($C_{1-4}$ alkyl)phenylsilyl, diphenyl($C_{1-4}$ alkyl)silyl, or triphenylsilyl, or both R together from an alkylidene protecting group;
R" is H, acetyl, benzyl, methoxymethyl, tosyl, mesyl, trifluoromesyl, tri($C_{1-4}$ alkyl)silyl, di($C_{1-4}$ alkylsilyl) phenylsilyl, diphenyl($C_{1-4}$ alkyl)silyl, or triphenylsilyl;
X is H, Cl, Br, or $R^4$ (where $R^4$ is $C_{1-22}$-alkyl);
Y is H, Cl, Br, or —$CHR^2OH$, —$CR^2R^3OH$, —$CH_2CHR^2OH$, —$CH_2CR^2R^3OH$, —$SR^2$, —$SeR^2$, —OH, —$NH_2$, —$R^5$ (where $R^2$, $R^3$, and $R^5$ are independently of each other $C_{1-22}$-alkyl);
or X and Y together form a covalent bond;
A and A' are both H or together A and A' form =O,
are useful as anticancer agents and as glycosidase inhibitors.

11 Claims, No Drawings

OTHER PUBLICATIONS

Pearson et al, *Tetrahedron Lett.*, vol. 31, pp. 7571–7574 (1990).
Miller et al, *J. Am. Chem. Soc.*, vol. 112, pp. 8100–8112 (1990).
Ikota et al, *Chem. Pharm. Bull.*, vol. 38, pp. 2712–2718 (1990).
Naruse et al, *J. Org. Chem.*, vol. 59, pp. 1358–1364 (1994).
Hunt et al, *Tetrahedron Lett.*, vol. 36, pp. 501–504 (1995).
Kang et al, *Tetrahedron Lett.*, vol. 36, pp. 5049–5052 (1995).
Oishi et al, *Synlett*, pp. 404–406 (1995).
Gonzalez et al, *Bull. Chem. Soc. Jpn.*, vol. 65, pp. 567–574 (1992).
Honda et al, *J. Chem. Soc., Perkin Trans. 1*, pp. 2091–2101 (1994).
Angermann et al, *Synlett*, pp. 1014–1016 (1995).
Zhou et al, *Tetrahedron Lett.*, vol. 36, pp. 1291–1294 (1995).*
Zhou et al, *Chem. Soc., Perkin Trans. 1*, pp. 2599–2604 (1995).*
Kim et al, *Tetrahedron Lett.*, vol. 30, pp. 5721–5724 (1989).*
Ina et al, *J. Org. Chem.*, vol. 58, pp. 52–61 (1993).*
Jirousek et al, *Tetrahedron Lett.*, vol. 34, pp. 3671–3674 (1993).*
Kim et al, *J. Org. Chem.*, vol. 58, pp. 7096–7099 (1993).*
Poitout et al, *Tetrahedron Lett.*, vol. 35, pp. 3293–3296 (1994).*
Lohray et al, *J. Org. Chem.*, vol. 60, pp. 5958–5960 (1995).*
Cohen et al, *J. Am. Chem. Soc.*, vol. 105, pp. 3661–3672 (1983).*
Cohen et al, in *Organic Synthesis*, Collective vol. VII, J. P. Freeman, Ed., Wiley: New York, pp. 297–301 (1990).*
Dunigan et al, *J. Org. Chem.*, vol. 56, pp. 6225–6227 (1991).*
Mekki et al, *Tetrahedron Lett.*, vol. 32, pp. 5143–5146 (1991).*
Johnson et al, *J. Am. Chem. Soc.*, vol. 92, pp. 741–743 (1970).*
Sharpless et al, *J. Org. Chem.*, vol. 57, pp. 2768–2771 (1992).*
Wang et al, *Tetrahedron Lett.*, vol. 33, pp. 6407–6410 (1992).*
Keinan et al, *Tetrahedron Lett.*, vol. 33, pp. 6411–6414 (1992).*
Keck, *J. Org. Chem.*, vol. 58, pp. 6083–6089 (1993).*
Still et al, *J. Org. Chem.*, vol. 43, pp. 2923–2925 (1978).*
Pearson et al, *J. Org. Chem.*, vol. 56, pp. 1976–1978 (1991).*

* cited by examiner

SWAINSONINE DERIVATIVES AND METHODS FOR PREPARING THE SAME

This application claims priority to U.S. Provisional Application No. 60/054,870, filed Aug. 6, 1997.

This invention was made with government support under Grant No. GM-35572 awarded by the National Institutes of Health. The government has certain rights in the invention.

BACKGROUND OF THE INVENTION

1. Field of the Invention

The present invention relates to derivatives of swainsonine, which are useful as anticancer agents and as glycosidase inhibitors. The present invention also relates to methods of preparing such derivatives and intermediates useful for preparing said derivatives.

2. Discussion of the Background

The indolizidine alkaloid (−)-swainsonine is of long standing interest due to its diverse biological activity. For the isolation from the fungus *Rhizoctonia leguminicola*, see:

(a) Guengerich, F. P. et al, *J. Am. Chem.* Soc., vol. 95, p. 2055 (1973).

(b) Schneider, J. J. et al. *Tetrahedron*, vol. 39, pp. 29–32 (1983).

(c) Hino, M. et al, *J. Antibiot.*, vol. 35, pp. 926–935 (1985).

(d) Patrick, M. S. et al, *Biotechnol. Lett.*, vol. 17, pp. 433–438 (1995).

For the isolation from the legume *Swainsona canescens*, see:

(e) Colegate, S. M. et al, *Aust. J. Chem.*, vol. 32, pp. 2257–64 (1979).

For the isolation from the locoweed *Astragalus lentiginosus*, see:

(f) Molyneux, R. J., *Science*, vol. 216, pp. 190–191 (1982).

For the isolation from Weir vine, see:

(g) Molyneux, R. J., *J. Nat. Prod.*, vol. 58, pp. 878–886 (1995).

For a review of the synthesis and biological activity of swainsonine and other glycosidase inhibitors, see:

Nishimura. Y. In *Studies in Natural Products Chemistry*; Atta-ur-Rahmaii, Ed.; Elsevier: Amsterdam, vol. 10; pp. 495–583 (1992).

(−)-Swainsonine may be considered an azasugar analog of mannose, and is indeed a potent inhibitor of many mannosidases including the glycoprotein processing enzyme mannosidase II (see: Elbein, A. D., *Ann. Rev. Biochem.*, vol. 56, pp. 497–534 (1987); Cenci Di Bello, I. et al, *Biochem. J.*, vol. 259. pp. 855–861 (1989); Winchester, B. et al; *Glycbiology*, vol. 2, pp. 199–210 (1992); and Kaushal G. P. et al, *Methods in Enzymology*, vol. 230, pp. 316–329 (1994)). Swainsonine is the first glycoprotein-processing inhibitor to be selected for clinical testing as an anticancer drug (see: Goss, P. E. et al *Clin. Cancer Res.*, vol. 1, pp. 935–944 (1995); and Das, P. C. et al, *Oncol. Res.*, vol. 7, pp. 425–433 (1995)).

A great deal of effort has been expended on developing synthetic routes to swainsonine. See e.g., (a) Suami, T. et al, *Chem. Lett.*, pp. 513–516 (1984).

(b) Ali, M. H. et al, *J. Chem. Soc., Chem. Commun.*, 447–448 (1984).

(c) Fleet, G. W. J. et al, *Tetrahedron Lett.*, vol. 25, pp. 1853–1856 (1984).

(d) Yasuda, N. et al, *Chem. Lett.*, pp. 1201–1204(1984).

(e) Adams, C. E. et al, *J. Org. Chem.*, vol. 50, pp. 420–422 (1985).

(f) Suami, T., *Carbohydr. Res.*, vol. 136, pp. 67–75 (1985).

(g) Ali, M. H. et al, *Carbohydr. Res.*, vol. 136, pp. 225–240 (1985).

(h) Setoi, H. et al, *J. Org. Chem.*, vol. 50, pp. 3948–3950 (1985).

(i) Ikota, N. et al, *Chem. Pharm. Bull.*, vol. 35, pp. 2140–25143 (1987).

(j) Ikota, N., et al, *Heterocycles*, vol. 26, p. 2368 (1987).

(k) Bashyal, B. P. et al, *Tetrahedron*, vol. 43, p. 3083 (1987).

(l) Dener, J. M. et al, *J. Org. Chem.*, vol. 53, pp. 6022–6030 (1988).

(m) Carpenter, N. M. et al, *Tetrahedron Lett.*, vol. 30, pp. 7261–7264 (1989).

(n) Bennett, R. B. et al, *J. Am. Chem. Soc.*, vol. 111, pp. 2580–2582 (1989).

(o) Pearson, W. H. et al, *Tetrahedron Lett.*, vol. 31, p. 7571(1990).

(p) Miller, S. A., *J. Am. Chem. Soc.*, vol. 112, pp. 8100–8112 (1990).

(q) Ikota, N. et al, *Chem. Pharm. Bull.*, vol. 38, p. 2712 (1990).

(r) Fleet, G. W. J., U.S. Pat. No. 5,023,340 (1991).

(s) Naruse, M. et al, *J. Org. Chem.*, vol. 59, pp. 1358–1604 (1994).

(t) Hunt, J. A. et al, *Tetrahedron Lett.*, vol. 36, pp. 501–504 (1995).

(u) Kang, S. H. et al. *Tetrahedron Lett.*, vol. 36, pp. 5049–5052 (1995).

For a synthesis of the non-natural (+)-enantiomer of swainsonine, see:

(v) Oishi. T. et al, *Synlett.*, pp. 404–406 (1995).

For formal syntheses, see:

(w) Gonzalez, F. B. et al, *Bull. Chem. Soc. Jpn.*, vol. 65. pp. 567–574 (1992).

(x) Honda, T., et al. *J. Chem. Soc., Perkin Trans.*, vol. 1, pp. 2091–2101 (1994).

(y) Angermann, J. et al, *Sylett*, pp. 1014–1016 (1995).

(z) Zhou, W.-S. et al, *Tetrahedron Lett.*, vol. 36, pp. 1291–1294 (1995).

(aa) Zhou, W.-S. et al, *J. Chem. Soc. Perkin Trans.*, vol. 1, pp. 2599–2604 (1995).

However, there is still a need for other compounds which exhibit similar anticancer and glycosidase inhibition properties as swainsonine.

Thus, there remains a need for compounds which exhibit anticancer activity. There also remains a need for compounds which inhibit glycosidase enzymes. There also remains a need for intermediates and methods useful for preparing such compounds.

SUMMARY OF THE INVENTION

Accordingly, it is one object of the present invention to provide novel compounds which are useful as anticancer agents.

It is another object of the present invention to provide novel compounds which are useful as glycosidase inhibitors.

It is another object of the present invention to provide novel intermediates useful for preparing such compounds.

It is another object of the present invention to provide a method for preparing such compounds.

These and other objects, which will become apparent during the following detailed description, have been achieved by the inventors discovery that compounds of the formula (I):

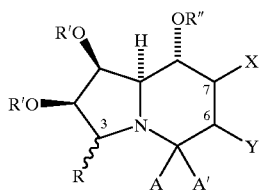

(I)

where:
R is:
  straight chain $C_{1-22}$-alkyl;
  branched $C_{3-22}$-alkyl;
  $C_{3-8}$-cycloalkyl;
  $C_{3-8}$-cycloalkyl substituted with straight chain $C_{1-22}$-alkyl;
  $C_{3-8}$-cycloalkyl substituted with branched $C_{3-22}$-alkyl;
  a group of the formula

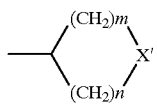

wherein:
    X'=O, S, NH, $NR^1$ ($R^1$ is $C_{1-22}$-alkyl), or NAr;
    m=0–5;
    n=0–5; and
    m+n≧2;
  —$(CH_2)_{n'}Ar$ (n'=1 to 22);
  —$(CH_2)_{n'}G$ (n'=1 to 22);
  —Ar; and
  —G;
  wherein Ar is:

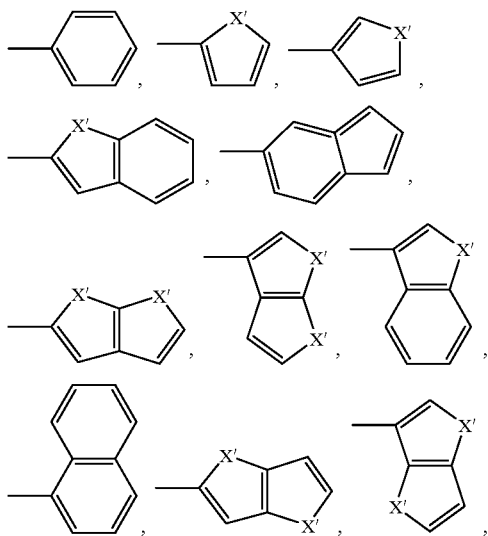

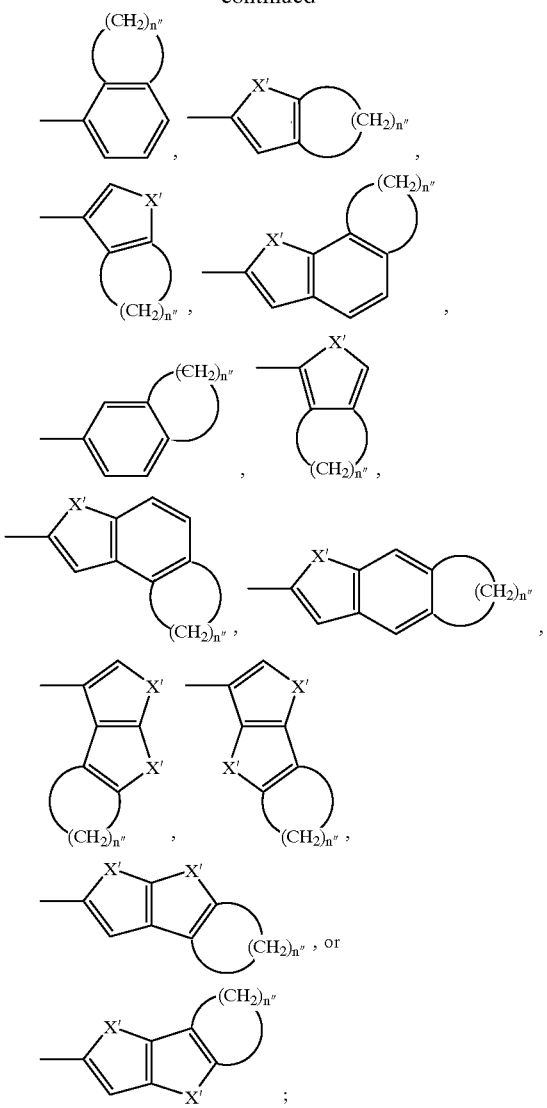

where
n"=2 to 5;
X'=NH, $NR^1$ ($R^1$ is $C_{1-22}$-alkyl), NAr, O, or S and each carbon atom may be substituted with halogen, $C_{1-22}$-alkyl, $C_{6-10}$-aryl, or G;
wherein G is:
  F, Cl, Br, I,
  —OH, —$OR^1$, —OCHO, —$OCOR^1$, —$OCO_2R^1$, —$OCONH_2$, —$OCONHR^1$, $OCONR^1R^1$, $OCOSR^1$, —$ONH_2$, —$ONHR^1$, —$ONR^1R^1$;
  —$N_3$, —$NO_2$, —$NH_2$, —$NHR^1$, —$NR^1R^1$, —NHOH, —$NR^1OH$, —$NHOR^1$, —$NR^1OR^1$, —$NHNH_2$, —$NR^1NH_2$, —$NHNHR^1$, —$NR^1NHR^1$, —$NHNR^1R^1$, —$NR^1NR^1R^1$, —NHC(=O)H, —$NR^1(C=O)H$, —NH(C=O) $R^1$, —$NR^1(C=O)R^2$, —NH(C=O)$OR^1$, —$NR^1$(C=O)$OR^2$, —NH(C=O)$NH_2$, —NH(C=O)$NHR^1$, —NH(C=O)$NR^1R^1$, —$NR^1(C=O)NH_2$, —$NR^1(C=O)NHR^2$, —$NR^1(C=O)NR^2R^3$, —NH(C=NH)$NH_2$, —$NR^1(C=NH)NH_2$, —NH(C=NH)$NHR^1$, —$NR^1(C=NH)NHR^2$, —NH(C=NH)$R^1R^2$, —$NR^1(C=NH)NR^2R^3$, —NH(C=$NR^1$)$NHR^2$, —$NR^1(C=NR^1)NHR^3$, —NH(C=$NR^1$)$NR^2R^3$, —$NR^1(C=NR^2)NR^3R^4$, —SH, SR¹, —S(C=O)R, —S(C=O)OR¹, —S(O)R¹, —SO₂R¹, —SO₃R¹, —SO₃H,
—SeR¹,
—CN, —CHO, —COR¹, —CHNOH, —CHNOR¹, —CR¹NOH, —CR¹NHOR², —CN, —CO₂H, —CO₂R¹, —CONH₂, —CONHR¹, —CONR¹R², —CSNH₂, —CSNHR¹, —CSNR¹R², —C(NH)OR¹, —C(NR)OR¹, —C(NH)SR¹, —C(NR)SR¹, —(NH)NH₂, —C(NR¹)NH₂, —C(NH)NR¹R², —C(NR)R¹R², —C(NR¹)NHR², —CONHOH, —CONR¹OH, —CONHOR¹, —CONR¹OR², —CONHNH₂, —CONR¹NH₂, —CONHNR¹R¹, —CONR¹NHR², -or CONR¹NR²R³,
(wherein $R^1$, $R^2$, and $R^3$ are each independently $C_{1-22}$-alkyl);

each $R^1$, independently of the other, is H, acetyl, benzyl, methoxymethyl, tosyl, mesyl, trifluoromesyl, tri($C_{1-4}$ alkyl)silyl, di($C_{1-4}$ alkyl)phenylsilyl, diphenyl($C_{1-4}$ alkyl)silyl, or triphenylsilyl, or both R together form an alkylidene protecting group;

R" is H, acetyl, benzyl, methoxymethyl, tosyl, mesyl, trifluoromesyl, tri($C_{1-4}$ alkyl)silyl, di($C_{1-4}$ alkylsilyl) phenylsilyl, diphenyl($C_{1-4}$ alkyl)silyl, or triphenylsilyl;

X is H, Cl, Br, or $R^4$ (where $R^4$ is $C_{1-22}$-alkyl);

Y is H, Cl, Br, or —CHR²OH, —CR²R³OH, —CH₂CHR²OH, —CH₂CR²R³OH, —SR², —SeR², —OH, —NH₂, —R⁵ (where $R^2$, $R^3$, and $R^5$ are independently of each other $C_{1-22}$-alkyl);

or X and Y together form a covalent bond;

A and A' are both H or together A and A' form =O are useful as anticancer agents and glycosidase inhibitors.

The inventors have also discovered that such compounds may be prepared from the compound of formula (II):

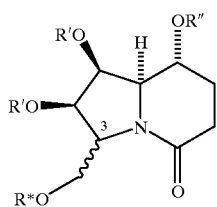

(II)

where R' and R" are the same as in compound (I) and R* is
straight chain $C_{1-22}$-alkyl;
branched $C_{3-22}$-alkyl;
$C_{3-8}$-cycloalkyl;
$C_{3-8}$-cycloalkyl substituted with straight chain $C_{1-22}$-alkyl;
$C_{3-8}$-cycloalkyl substituted with branched $C_{3-22}$-alkyl;
a group of the formula

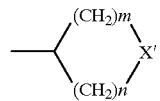

wherein:
X'=O, S, NH, NR¹ ($R^1$ is $C_{1-22}$-alkyl) or NAr;
m=0–5;
n=0–5; and
m+n≧2;
—(CH₂)ₙ'Ar (n'=1 to 22);
—(CH₂)ₙ'G (n'=1 to 22);
—Ar; and
—G;
wherein Ar is:

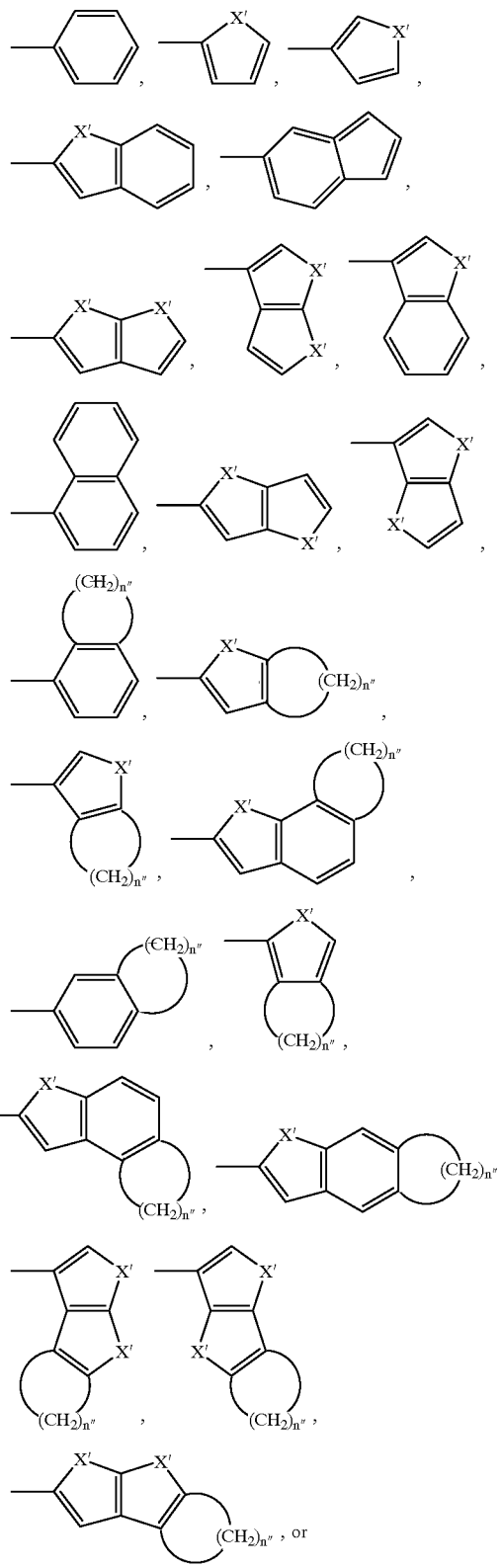

-continued

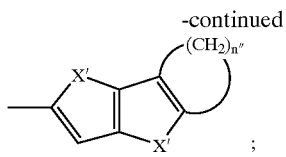

where
n"=2 to 5;
X'=NH, NR$^1$ (R$^1$ is C$_{1-22}$-alkyl), NAr, O, or S and each carbon atom may be substituted with halogen, C$_{1-22}$-alkyl, C$_{6-10}$-aryl, or G;
wherein G is:
F, Cl, Br, I, —CN, —CHO, —COR$^1$, —CHNOH, —CHNOR$^1$, —CR$^1$NOH, —CR$^1$NHOR$^2$, —CN, —CO$_2$H, —CO$_2$R$^1$, —CONH$_2$, —CONHR$^1$, —CONR$^1$R$^2$, —CSNH$_2$, —CSNHR$^1$, —CSNR$^1$R$^2$, —C(NH)OR$^1$, —C(NR)OR$^1$, —C(NH)SR$^1$, —C(NR)SR$^1$, —C(NH)NH$_2$, —C(NR$^1$)NH$_2$, —C(NH)NR$^1$R$^2$, —C(NR)R$^1$R$^2$, —C(NR$^1$)NHR$^2$, —CONHOH, —CONR$^1$OH, —CONHOR$^1$, —CONR$^1$OR$^2$, —CONHNH$_2$, —CONR$^1$NH$_2$, —CONHNR$^1$R$^2$, —CONR$^1$NHR$^2$, -or CONR$^1$NR$^2$R$^3$,
(wherein R$^1$, R$^2$ and R$^3$ are each independently C$_{1-22}$-alkyl).

DETAILED DESCRIPTION OF THE
PREFERRED EMBODIMENTS

Thus, in a first embodiment, the present invention provides novel compound of the formula:

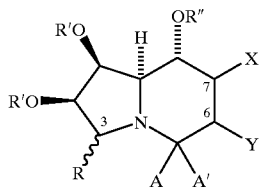

(I)

where:
R is:
  straight chain C$_{1-22}$-alkyl;
  branched C$_{3-22}$-alkyl;
  C$_{3-8}$-cycloalkyl;
  C$_{3-8}$-cycloalkyl substituted with straight chain C$_{1-22}$-alkyl;
  C$_{3-8}$-cycloalkyl substituted with branched C$_{1-22}$-alkyl;
  a group of the formula

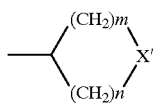

wherein:
X'=O, S, NH, NR$^1$ (R$^1$ is C$_{1-22}$-alkyl), or NAr;
m=0–5;
n=0–5; and
m+n≥2;
—(CH$_2$)$_{n'}$Ar (n'=1 to 22);
—(CH$_2$)$_{n'}$G (n'=1 to 22);
—Ar; and
—G;

wherein Ar is:

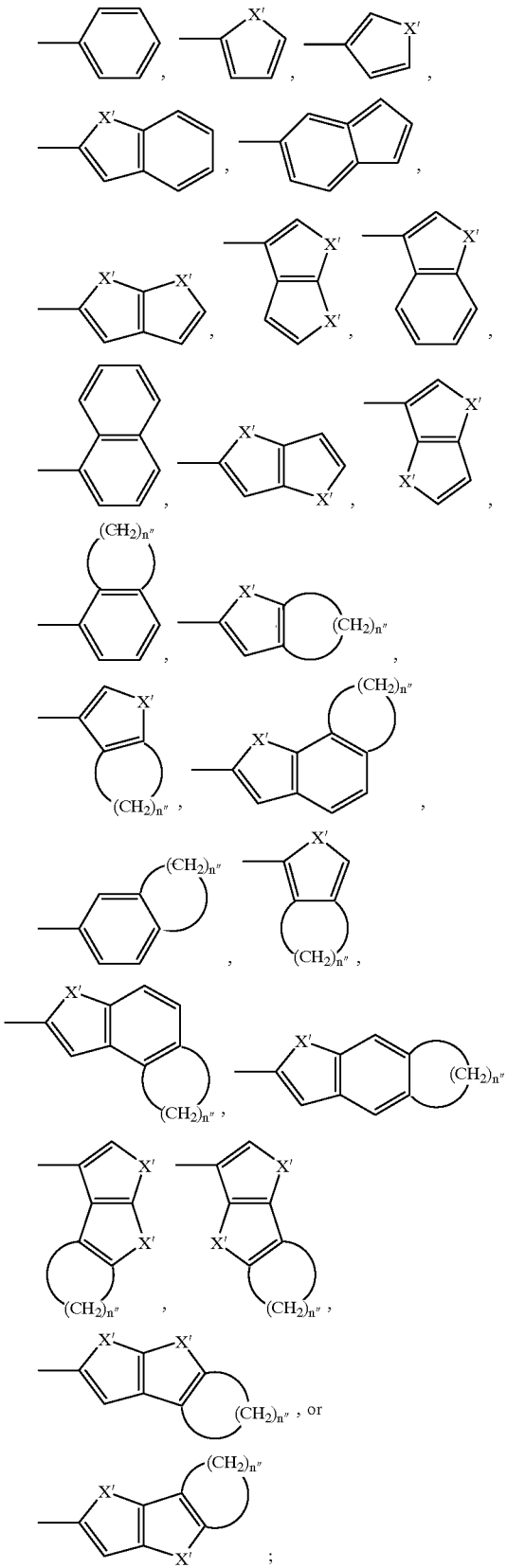

where
n"=2 to 5;
X'=NH, NR$^1$ (R$^1$ is C$_{1-22}$-alkyl), NAr, O or S
and each carbon atom may be substituted with halogen, C$_{1-22}$-alkyl, C$_{6-10}$-aryl, or G;
wherein G is:
F, Cl, Br, I,
—OH, —OR$^1$, —OCHO, —OCOR$^1$, —OCO$_2$R$^1$, —OCONH$_2$, —OCONHR$^1$, OCONR$^1$R$^1$, OCOSR$^1$, —ONH$_2$, —ONHR$^1$, —ONR$^1$R$^1$;
—N$_3$, —NO$_2$, —NH$_2$, —NHR$^1$, —NR$^1$R$^1$, —NHOH, —NR$^1$OH, —NHOR$^1$, —NR$^1$OR$^1$, —NHNH$_2$, —NR$^1$NH$_2$, —NHNHR$^1$, —NR$^1$NHR$^1$, —NHNR$^1$R$^1$, —NR$^1$NR$^1$R$^1$, —NHC(=O)H, —NR$^1$(C=O)H, —NH(C=O)R$^1$, —NR$^1$(C=O)R$^2$, —NH(C=O)OR$^1$, —NR$^1$(C=O)OR$^2$, —NH(C=O)NH$_2$, —NH(C=O)NHR$^1$, —NH(C=O)NR$^1$R$^2$, —NR$^1$(C=O)NH$_2$, —NR$^1$(C=O)NHR$^2$, —NR$^1$(C=O)NR$^2$R$^3$, —NH(C=NH)NH$_2$, —NR$^1$(C=NH)NH$_2$, —NH(C=NH)NHR$^1$, —NR$^1$(C=NH)NHR$^2$, —NH(C=NH)R$^1$R$^2$, —NR$^1$(C=NH)NR$^2$R$^3$, —NH(C=NR$^1$)NHR$^2$, —NR$^1$(C=NR$^2$)NHR$^3$, —NH(C=NR$^1$)NR$^2$R$^3$, —NR$^1$(C=NR$^2$)NR$^3$R$^4$,
—SH, SR$^1$, —S(C=O)R, —S(C=O)OR$^1$, —S(O)R$^1$, —SO$_2$R$^1$, —SO$_3$R$^1$, —SO$_3$H, —SeR$^1$,
—CN, —CHO, —COR$^1$, —CHNOH, —CHNOR$^1$, —CR$^1$NOH, —CR$^1$NHOR$^2$, —CN, —CO$_2$H, —CO$_2$R$^1$, —CONH$_2$, —CONHR$^1$, —CONR$^1$R$^2$, —CSNH$_2$, —CSNHR$^1$, —CSNR$^1$R$^2$, —C(NH)OR$^1$, —C(NR)OR$^1$, —C(NH)SR$^1$, —C(NR)SR$^1$, —C(NH)NH$_2$, —C(NR$^1$)NH$_2$, —C(NH)NR$^1$R$^2$, —C(NR)R$^1$R$^2$, —C(NR$^1$)NHR$^2$, —CONHOH, —CONR$^1$OH, —CONHOR$^1$, —CONR$^1$OR$^2$, —CONHNH$_2$, —CONR$^1$NH$_2$, —CONHNR$^1$R$^2$, —CONR$^1$NHR$^2$, -or CONR$^1$NR$^2$R$^3$,
(wherein R$^1$, R$^2$, and R$^3$ are each independently C$_{1-22}$-alkyl);
each R', independently of the other, is H, acetyl, benzyl, methoxymethyl, tosyl, mesyl, trifluoromesyl, tri(C$_{1-4}$ alkyl)silyl, di(C$_{1-4}$ alkyl)phenylsilyl, diphenyl(C$_{1-4}$ alkyl)silyl or triphenylsilyl, or both R together form an alkylidene protecting group;
R" is H, acetyl, benzyl, methoxymethyl, tosyl, mesyl, trifluoromesyl, tri(C$_{1-4}$ alkyl)silyl, di(C$_{1-4}$ alkylsilyl) phenylsilyl, diphenyl(C$_{1-4}$ alkyl)silyl, or triphenylsilyl;
X is H, Cl, Br, or R$^4$ (where R$^4$ is C$_{1-22}$-alkyl);
Y is H, Cl, Br, or —CHR$^2$OH, —CR$^2$R$^3$OH, —CH$_2$CHR$^2$OH, —CH$_2$CR$^2$R$^3$OH, —SR$^2$, —SeR$^2$, —OH, —NH$_2$, —R$^5$ (where R$^2$, R$^3$, and R$^5$ are independently of each other C$_{1-22}$-alkyl);
or X and Y together form a covalent bond;
A and A' are both H or together A and A' form =O.

One set of preferred compounds includes those compounds in which A and A' are both H. Another preferred set of compounds includes those compounds in which both X and Y are H. Another preferred set of compounds includes those compounds in which A, A', X and Y are all H.

The compounds of formula (I) in which A and A' are both hydrogen may be prepared from the compound of formula (II), by reduction of the carbonyl group. This reduction may be conveniently carried out using BH$_3$.SMe$_2$.

The compounds of formula (I) in which X and Y are not both hydrogen may be prepared by two different methods. In the first method, the compound of formula (II) is treated with a strong base in an inert solvent to form the enolate of formula (III).

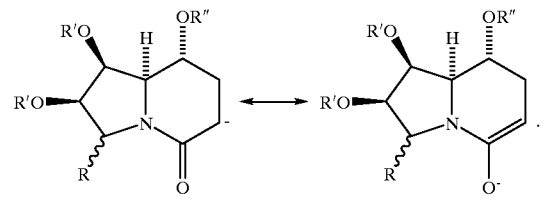

Suitable bases and solvents for the formation of the enolate of formula (III) include i-Pr$_2$NLi, s-BuLi, n-BuLi, t-BuLi, LiSi(Me)$_3$, KSi(Me)$_3$, and NaSi(Me)$_3$.

When forming the enolate of formula (III), it is preferred that R" not be hydrogen. It is particularly preferred that R" be a silyl protecting group. However, it is possible to form the enolate even when R" is hydrogen by using two equivalents of base:

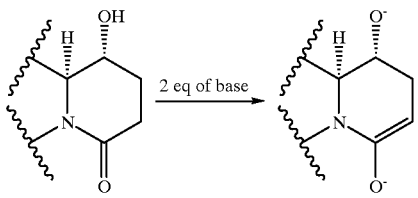

This dianion may be used successfully in further reactions of the enolate; the electrophile does not react at the oxygen atom.

Various compounds of the formula (I) in which X is H may be prepared by reacting the enolate of formula (III) with the reagents shown in the Table below:

| Y | Reagent[1] |
|---|---|
| —R$^2$ | R$^2$—L |
| ![OH; —C(H)(R$^2$)—] | ![R$^2$C(=O)H] |
| ![OH; —C(R$^3$)(R$^2$)—] | ![R$^2$C(=O)R$^3$] |
| —CH$_2$—CH(OH)R$^2$ | ![epoxide with R$^2$] |
| —CH$_2$—C(OH)(R$^2$)(R$^3$) | ![epoxide with R$^2$, R$^3$] |
| —SR$^2$ | R$^2$SL |
| —SeR$^2$ | R$^2$SeL |

-continued

| Y | Reagent[1] |
|---|---|
| —OH | O\O C(CH_3)(CH_3) |
| —NH_2 | 1) t-BuO_2C—N=N—CO_2-t-Bu<br>2) H_2, Pd—C<br>3) CF_3CO_2H |

[1]These reactions may be carried out as described in B. Trost, et. al, Comprehensive Organic Synthesis, Pergamon Press, 1991. $R^2$ and $R^3$ are independently of each other $C_{1-22}$-alkyl and L is a leaving group, such as, e.g., Cl.

The second method for preparing compounds in which X and Y are not both H involves the formation of the α,β-unsaturated enone of formula (IV)

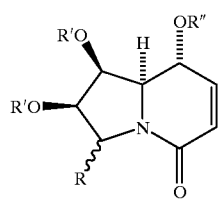

(IV)

where R, R', and R" are as defined above. The α,β-unsaturated enone of formula (IV) may be formed by oxidizing the compound of formula (I) in which R' and R" are not H; A and A' together are =O, X is H, and Y is ~SePh or ~SPh with m-chloroperoxybenzoic acid (mCPBA) or any other suitable oxidant and then heating the product:

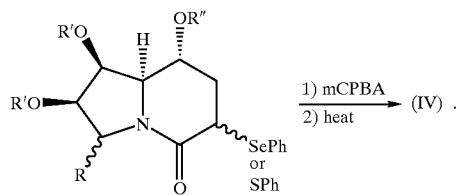

The α,β-unsaturated enone of formula (IV) may then be reacted with a reagent to afford compounds of formula (I) in which X and Y are not both H as shown in the Table below.

| X | Y | Reagent[2] |
|---|---|---|
| —R[4] | H | 1) R[4]_2CuLi or similar cuprate<br>2) H_2O |
| —R[4] | —R[5] | 1) R[4]_2CuLi or similar cuprate<br>2) R[5]—X |
| —R[4] | OH<br>\|<br>——CH——R[5] | 1) R[4]_2CuLi or similar cuprate<br>2) R[5]CHO |
| —R[4] | —SR[5] | 1) R[4]_2CuLi or similar cuprate<br>2) R[5]SL |
| —R[4] | —SeR[5] | 1) R[4]_2CuLi or similar cuprate<br>2) R[5]SeL |
| —R[4] | —OH | 1) R[4]_2CuLi or similar cuprate |

-continued

| X | Y | Reagent[2] |
|---|---|---|
| | | 2) O\O C(CH_3)(CH_3) |
| —R[4] | —NH_2 | 1) R[4]_2CuLi or similar cuprate<br>2) t-BuO_2CN=NCO_2-t-Bu<br>3) H_2, Pd<br>4) CF_3CO_2H |
| —R[4] | —CH_2CH(OH)R[5] | 1) R[4]_2CuLi or similar cuprate<br>2) 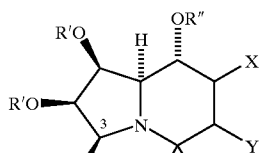 |
| —R[4] | —CH_2C(OH)R[5]R[6] | 1) R[4]_2CuLi or similar cuprate<br>2) 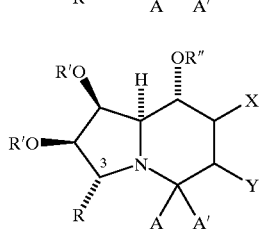 |

[2]These reactions may be carried out as described in B. Trost, et. al, Comprehensive Organic Synthesis, Pergamon Press, 1991. $R^4$, $R^5$, and $R^6$ are independently of each other $C_{1-22}$-alkyl and L is a leaving group, such as, e.g., Cl.

In formula (I) the stereochemistry of the attachment of R to carbon atom 3 is unspecified. It is to be understood that formula (I) covers both possible stereoisomers, as well as mixtures thereof. Thus, the present invention encompasses the compounds of formulae (Ia) and (Ib), and mixtures thereof.

(Ia)

(Ib)

The compounds of formula (Ia) and (Ib) can be prepared from the corresponding enolates and α,β-unsaturated enones having the same stereochemistry at carbon atom 3. The enolates and α,β-unsaturated enones are in turn prepared from the two corresponding stereoisomers of the compound of formula (II), referred to as (IIa) and (IIb).

The compounds of formula (IIa) may be prepared by catalytic hydrogenation of the compound of formula (V) followed by heating with methanolic sodium methoxide as shown below:

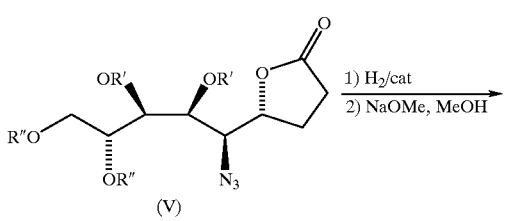

The compounds of formula (IIb) may be prepared by catalytic hydrogenation of the compound of formula (VI) followed by heating with methanolic sodium methoxide as shown below:

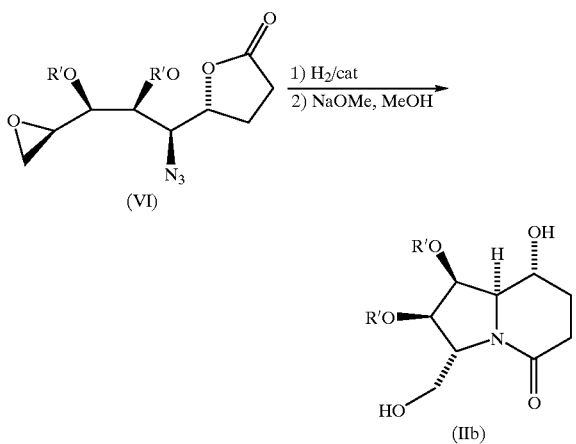

The compound of formula (IIa) may be treated with a variety of reagents to afford the different R groups, as shown in the Table below:

| R | Reagent[3] |
|---|---|
| HOCH$_2$- | No Treament Required |
| ClCH$_2$- | PPh$_3$, CCl$_4$ |
| BrCH$_2$- | PPh$_3$, CBr$_4$ |
| R$^7$OCH$_2$- | R$^7$L, base |
| TsOCH$_2$- | TsCl, Pyridine |
| MsOCH$_2$- | MsCl, NEt$_3$ |
| TBSOCH$_2$- | TBSCl, imidazole |
| TMSOCH$_2$- | TMSCl, imidazole |
| AcOCH$_2$ | Ac$_2$O, pyridine |
| BzOCH$_2$- | BzCl, pyridine |
| HC(=O)- | (COCl)$_2$, NEt$_3$, DMSO |
| HOC(=O)- | PDC |
| R$^7$OC(=O)- | 1) PDC, 2) ROH, 3) DCC |
| ArOC(=O)- | 1) PDC, 2) ArOH, 3) DCC |

[3]These reactions may be carried out as described in B. Trost, et al, ComprehensiveOrganicSynthesis, Pergamon Press, 1991. R$^7$ is C$_{1-22}$-alkyl and L is a leaving group, such as, e.g., Cl.

The compounds of formula (IIb) may be reacted with the same reagents as described in the context of formula (IIa) to afford the various R groups.

The compounds of formula (I) may be used as anticancer agents and glycosidase inhibitors in the same way as swainsonine itself, (see, e.g., Goss, P. E. et al, *Clin. Cancer Res.*, vol. 1, pp. 935–944 (1995); and Das. P. C. et al, *Oncol. Res.*, vol. 7, pp. 425–433 (1995), which are incorporated herein, by reference).

One of the major challenges in using azasugars inhibitors of glycosidase enzymes as biochemical tools or drugs is that they generally suffer from a lack of specificity (Tulsiani, D. R. P.; et al, *J. Biol. Chem.*, Vol. 257, pp. 7936–9 (1982); Kaushal, G. P.; et al, *Methods in Enzymology*, Vol. 230, pp. 316–329 (1994); and Goss, P. E. et al, *Clin. Cancer Res.* Vol. 1, pp. 935–944 (1995)). The pyrrolizidines 1–4 generally exhibit glucosidase inhibitory activity.

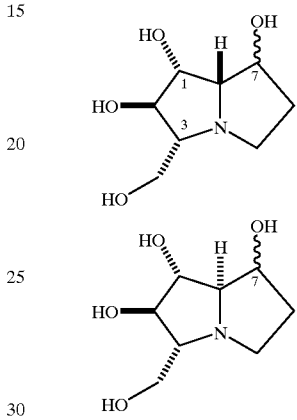

For example, 1, (Nash, R. J., et al, *Phytochemistry*, Vol. 29, pp. 111–1145 (1990); Scofield, A. M., et al, *Phytochemistry* Vol. 29, pp. 107–109 (1990)), 3 (Nash, R. J., et al, *Phytochemistry* Vol. 29. pp. 111–114 (1990); Molyneux, R. J., et al. *J. Nat. Prod.*, Vol. 51, pp. 198–1206 (1988); Tropea. J. E., et al, *Biochemistry*, Vol. 28, pp. 2027–2034 (1989)); and 4 (Nash, R. J., et al, *Phytochemistry*, Vol. 29, pp. 111–114 (1990); Molyneux, R. J., et al, *J. Nat. Prod.*, Vol. 51, pp. 1198–1206 (1988); Tropea, J. E., et al, *Biochemistry*, Vol. 28, pp. 2027–2034 (1989)) are good inhibitors of amyloglucosidase and glucosidase I (Tropea, J. E., et al, *Biochemistry*, Vol 28, pp. 2027–2034 (1989); Taylor, D. L., et al, *Antiviral Chem. Chemother.*, Vol. 3, pp. 273–277 (1992). These and other polydroxylted alkaloids show promising biological activity, e.g. 4 shows anti-HIV activity (Taylor, D. L., et al, *Antiviral Chem. Chemother.*, Vol. pp. 273–277 (1992)).

In contrast, the pyrrolizidine inhibitors 1–4 have not been reported to exhibit manuiosidase inhibitory activity. Most good mannosidase inhibitors are epimeric to 1–4 at the carbon corresponding to C(1) (Cenci Di Bello, I., et al, *Biochem. J.*, Vol. 259, pp. 855–861 (1989); Winchester. B., et al, *Biochem. J.*, Vol., 290, pp. 743–749 (1993)) for example swainsonine, the first glycoprotein-processing inhibitor to be selected for clinical testing, as an anticancer drug. (Goss, P. E., et al. *Cancer Res.*, Vol. 1, pp. 935–944 (1995); Das, P. C., et al, *Oncol. Res.*, Vol. 7, pp. 425–433 (1995); Nishimura, Y. In *Studies in Natural Products Chemistry*, Atta-ur-Ralmuan, Ed.; Elsevier: Amsterdam, 1992; Vol. 10; pp 495–583). This suggests that 3-hydroxymethyl-substituted swainsonine analogs, e.g. (3R)-(hydroxymethyl)swainsonine [10, (3R)-HMS] and (3E)-(hydroxymethyl)swainsonine [11, (3S)-HMS], might be potent mannosidase inhibitors and perhaps be useful as anticancer agents. Further, the hydroxymethyl substituents of 11, and especially 10, are expected to occupy the same region of space in the enzyme binding pocket that the anomeric substituent on a D-mannose residue does in the natural substrate. The hydroxymethyl oxygen of 10 or 11 could thus serve as a site of attachment for another sugar residue, or other sugar-like substituents, to afford disaccharide mimics that would more closely resemble the Man(α-1,3)Man or Man(α-1,6)Man linkage recognized and cleaved by the human glycoprotein processing enzyme maniosidase II, (Elbein, A. D., *FASEB J.*, Vol. 5, pp. 3055–3063 (1991); Elbeirn, A. D., et al. *Ann. Rev. Biochem*, Vol. 56, pp. 497–534 (1987)) hopefully resulting in more potent and selective inhibitors of this important enzyme. A number of disaccharide mimics involving other azasugar inhibitors are known and have been reported to be selective glycosidase inhibitors (Knapp, S., et al, *J. Am. Chem. Soc.*, Vol. 116, pp. 7461–7462 (1994); Kaushal, G. P., et al, *J. Biol. Chem.*, Vol. 263, pp. 17278–17283 (1988)).

The present invention will now be further described in the context of the synthesis of the (1S,2R,3R,8R,8aR)-3-(hydroxymethyl)-1,2,8-trihydroxyindolizidine and (1S,2R, 3S,8R,8aR)-3-(hydroxymethyl)-1,2,8-trihydroxyindolizidinie, the compounds of formulae (VII) and (VIII), respectively.

The synthesis of the two diastereomers (VII) and (VIII) began with 2,3-O-cyclohexylidene-D-ribose (XIII), prepared from D-ribose by the method of Mori and Kikuchi (Mori, K., et al, *Liebigs Ann. Chem.*, pp. 1267–1269 (1989)) (Scheme 1). Deprotonation of (XIII) followed by addition of vinylmagnesium bromide gave a triol, which was subjected to acetonide formation without purification, resulting in the formation of the allylic alcohol (XIV) as a single diastereomer, as judged by 300 MHZ $^1$H NMR spectroscopy. This outcome was expected, since the addition of vinylmagnesium bromide to 2,3-O-isopropylidene-D-ribose (Mekki, B., et al, *Tetrahedron Lett.*, Vol. 32. pp. 5143–5146 (1991)) and the addition of other Grignard reagents to (XIII) (Mori. K., et al, *Liebigs Ann. Chem.*, pp. 1267–1269 (1989)) have been reported to occur with high stereoselectivity. Johnson orthoester Claisen rearrangement (Johnson, W. S., et al. *J. Am. Chem. Soc.*, Vol. 92, 741–743 (1970)) of (XIV) proceeded smoothly to afford the γ,δ-unsaturated ester (XV), which was subjected without purification to Sharpless asymmetric dihydroxylation conditions (Sharpless, K. B. et al, *J. Org. Chem.*, Vol 57, pp. 2768–2771 (1992); Wang, Z.-M., et al, *Tetrahedron Lett.*, Vol. 33, pp. 6407–6410 (1992): Keinan, E., et al, *Tetrahedron Lett.*, Vol. 33, pp. 6411–6414 (1992)) The desired hydroxy lactone (XVI) was obtained in 66% overall yield from (XIV) by crystallization and chromatography, which also provided the minor isomer (XVII) in 6% yield. The double diasterodifferentiation afforded by the Sharpless dihydroxylation was necessary for this level of stereoselectvity. Mesylation of (XVI), followed by azide displacement, gave the azido lactone (XVIII). Selective hydrolysis of the acetonide group of (XVIII) in the presence of the cyclohexylidene group was possible with aqueous sulfuric acid. The best results were obtained by running the reaction to partial conversion; a substantial amount of tetraol was formed at full conversion. Selective silylation of the primary hydroxyl group of the diol (XIX), followed by mesylation of the secondary hydroxyl group, afforded the key azido mesylate (XX).

Scheme 1
Synthesis of the azido mesylate (XX)

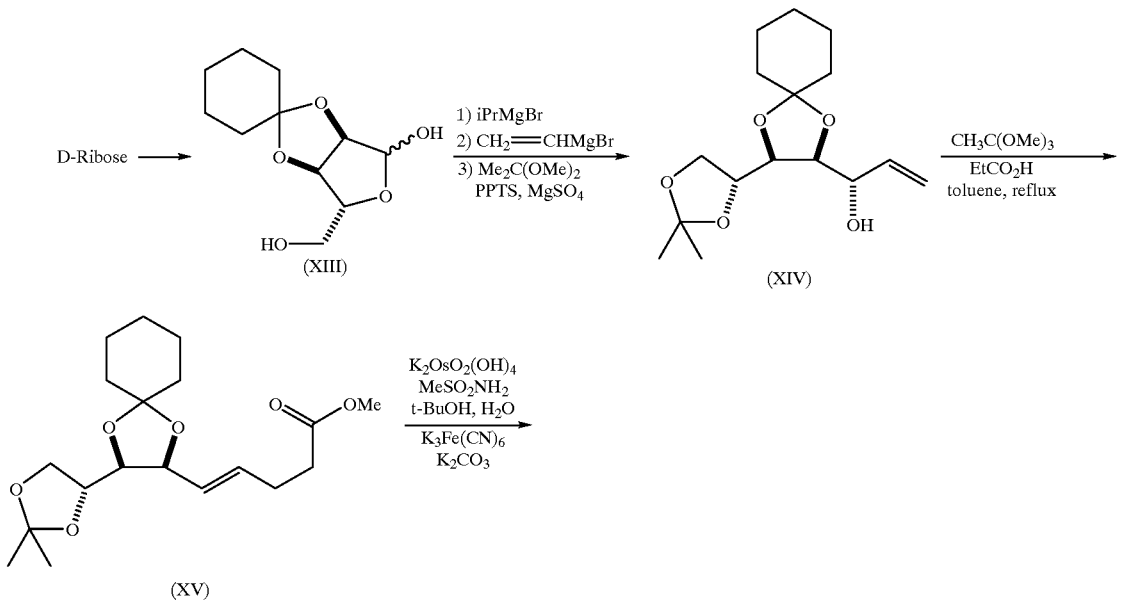

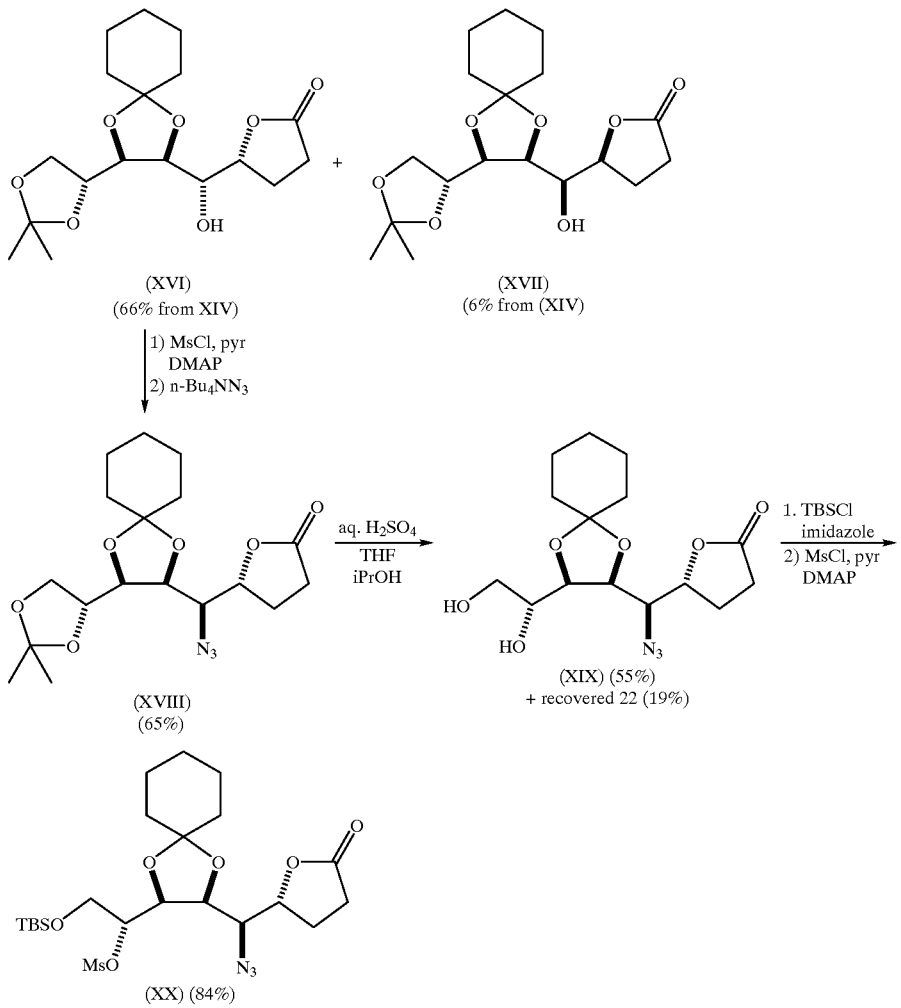

Completion of the synthesis of (VIII) is shown in Scheme 2. Catalytic hydrogenation of the azido mesylate (XX) generated a primary amine, which was alkylated in situ by the mesylate. The resultant pyrrolidino lactone was heated with methanolic sodium methoxide to promote N-acylation, affording the indolizidinone (XXI) in good yield. Borane reduction of (XXI) gave the indolizine (XXII), which was deprotected to produce (3S)-3-(hydroxymethyl)swainsonine (VIII). The synthesis of (VIII) from 2,3,-O-cyclohexylidene-D-ribose (XIII) proceeded in 8% overall yield, requiring 12 steps.

Scheme 2
Synthesis of (3S)-3(hydroxymethyl) swainsonine (VIII) by reductive double cyclization

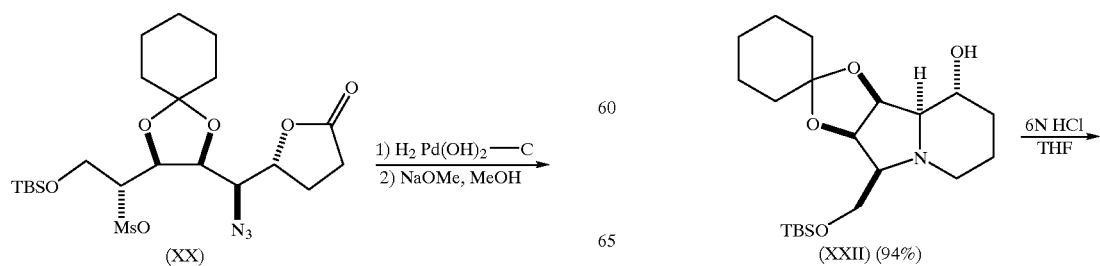

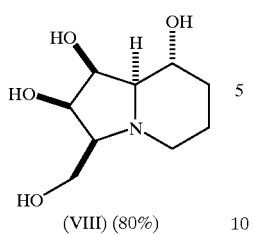

(VIII) (80%)

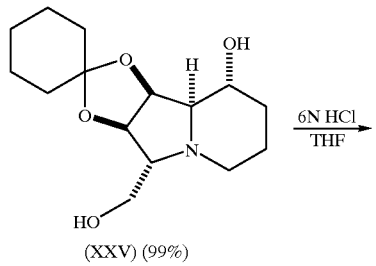

(XXV) (99%)

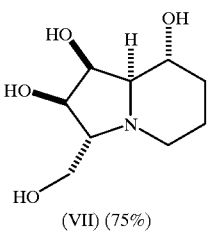

(VII) (75%)

The steps required to complete the synthesis of (VII) are shown in Scheme 3. Initial attempts to convert the azido mesylate (XX) to the epoxide (XXIII) using tetra-n-butylammonium fluoride led to poor results, affording mostly the hydroxy mesylate. However, the use of anhydrous cesium fluoride in warm acetonitrile provided the epoxide directly in high yield (Hünig, S., et al, *Chem. Ber.*, Vol. 123, pp. 107–114 (1990)). Reductive double-cyclization of the azido epoxide (XXIII) as described above provided the indolizidinone (XXIV). Reduction of (XXIV) with borane-methyl sulfide complex produced the indolizine (XXV), which was deprotected to afford (3R)-3-(hydroxymethyl)swainsonine (VII). The synthesis of (VII) from 2,3-O-cyclohexylidene-D-ribose (XIII) proceeded in 6% overall yield, requiring 13 steps.

Scheme 3
Synthesis of (3R)-3-(hydroxymethyl) swainsonine (VII) by reductive double cyclization

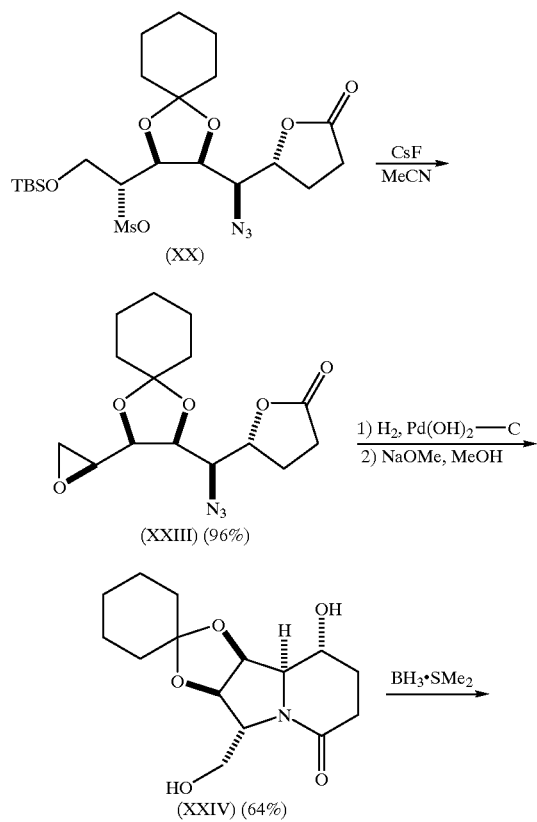

Initial screening in our laboratories using standard techniques (Tropea, J. E., et al *Biochemistry*, Vol. 28, pp. 2027–2034 (1989)) showed that the hydroxymethyl-substituted swainsonine analogs (VII) and (VIII) were indeed inhibitors of α-mannosidase (jack bean). As predicted, (VII), bearing an α-oriented hydroxymethyl group, was a better inhibitor, with an $IC_{50}$ of 1.2 $\mu$M versus 45 $\mu$M for (VIII), which bears a β-oriented hydroxymethyl group. These values compare with an $IC_{50}$ of 0.1 $\mu$M for swainsonine.

Other features of the invention will become apparent in the course of the following descriptions of exemplary embodiments which are given for illustration of the invention and are not intended to be limiting thereof.

EXAMPLES

General. All commercial reagents (if liquid) were distilled prior to use. All other solid reagents were used as obtained. Tetrahydrofuran was distilled from sodium/benzophenone ketyl. Toluene, benzene, dichloromethane, dimethyl sulfoxide, and triethylamine were distilled from calcium hydride. Dimethylformamide was distilled from barium oxide at reduced pressure. Methanol and ethanol were distilled from calcium oxide. Analytical thin layer chromatography (tlc) was conducted on precoated silica gel plates (Kieseigel 60 $F_{254}$, 0.25 mm thickness, manufactured by E. Merck & Co., Germany). For visualization, tlc plates were stained with iodine vapor or phosphomolybdic acid solution. Gas chromatographic (GC) analyses were performed using a 530$\mu$ methylpolysiloxane column (3$\mu$ film thickness, 5 m length) using flame ionization detection. A standard temperature program of 100° C. for 2 min followed by a 40° C./min ramp, to 200° C. was used. Elmental analyses were performed by the University of Michigan Department of Chemistry CHN/AA Services Branch. $^1$H NMR spectral assignments were made on the basis of two dimensional correlated off resonance spectroscopy (COSY) experiments. High resolution mass spectrometric (HRMS) measurements are accurate to within 2.2 ppm (electron impact, EI). 3.9 ppm (chemical ionization, CI). or 3.3 ppm (fast-atom bombardment, FAB), based on measurement of the performance of the mass spectrometer on a standard organic sample. Flash column chromatography was performed according to the general procedure described by Still (Still, W. C., et al, *J. Org. Chem.*, Vol. 43, pp. 2923–2925 (1978))

using flash grade Merck Silica Gel 60 (230–400 mesh). The enzyme α-mannosidase (from jack bean) and the corresponding p-nitrophenyl α-D-mannopyranoside substrate was obtained from Sigma Chemical Co. Enzyme inhibition was assayed colorimetrically by monitoring the release of p-nitrophenol from p-nitrophenyl α-D-mannopyranoside according to the procedure described by Tropea, et. al. (Tropea, J. E., et al, Biochemistry, Vol. 28, pp. 2027–2034 (1989)).

(2R,3R,4S,5S)-3,4-Cyclohexylidenedioxy-1,2-isopropylidenedioxy-6-hepten-5-ol (XIV)

Isopropylmagnesium bromide (131 mL of a 2 M solution in THF, 262 mmol) was added in a dropwise fashion via an addition funnel to a cooled (0° C.) solution of 2,3-O-cyclohexylidene-D-ribose (Mori, K., et al, *Liebigs Ann. Chem.*, pp. 1267–1269 (1989)) (40.3 g, 175 mmol) in THF (600 ml). After the addition was complete, the solution was allowed to stir for 15 min, then vinylmagnesium bromide (440 mL of a 1M solution in THF, 440 mmol) was added via an addition funnel over a period of 1 hour. After the addition was complete. the solution was allowed to warm to room temperature. After 12 hours, the solution was cooled back to 0° C., and was quenched by the addition of saturated aqueous $NH_4Cl$ (200 mL). The resulting mixture was diluted with water (500 mL) and extracted with EtOAc (3×500 mL). The organic layers were washed with brine, dried ($MgSO_4$), filtered, and concentrated to give 49.7 g of crude (2R,3R,4S,5S)-3,4-cyclohexylidenedioxy-1,2,5-trihydroxy-6-heptene as a yellow oil that was used without further purification. [$R_f$=0.09 (2:1 hexane/EtOAc); $^1$H NMR (300 MHZ, $CDCl_3$) δ6.04 (ddd, J=5.6, 10.6, 17.3 Hz, 1H), 5.38 (dt, J=1, 17.3 Hz, 1H), 5.27 (dt, J=1, 10.5 Hz, 1H), 4.69 (br s, 1H), 4.35 (m, 2H), 4.11 (dd, J=5.0, 8.8 Hz, 1H), 4.03 (dd, J=5.8, 8.8 Hz, 1H), 3.90 (m, 2H), 3.71 (m, 1H), 3.33 (brs, 1), 1.5–1.7 (m, 8H), 1.35 (m, 2H); $^{13}$C NMR (75 MHZ, $CDCl_3$) δ137.8, 116.3, 109.5, 79.8, 77.5, 70.7, 69.7, 64.6, 37.9, 35.0, 25.1, 24.1, 23.8.] The crude triol was dissolved in THF (500 mL) and 2,2-dimethoxypropane (55 g, 525 mmol), pyridinium p-toluenesulfonate (2.2 g, 8.8 mmol), and magnesium sulfate (10 g) were added. After 18 hours, the mixture was poured into ether (500 mL) and washed with saturated aqueous $NaHCO_3$ (300 mL) and brine (200 mL), then dried ($MgSO_4$), filtered, and concentrated. Only one stereoisomer of (XIV) was observed in the 300 MHz $^1$H NMR spectrum of the crude product. Chromatography (20:1 to 10:1 hex/EtOAc gradient) provided 36.5 g (70%) of the title compound, $R_f$=0.39 (6:1 hexane/EtOAc); $[α]^{23}_D$+1.9 (c 1.08, $CHCl_3$); $^1$H NMR (300 MHz, $CDCl_3$) δ6.07 (ddd, J=4.6, 10.7, 17.3 Hz, 1H), 5.46 (dt, J=1.8, 17.3 Hz, 1H) 5.24 (dt, J=1.8, 10.7 Hz, 1H), 4.36 (m, 1H), 4.20 (m, 2H), 4.04 (m, 3H) 3.91 (2, J=3.4 Hz, 1H), 1.5–1.65 (m, 8H), 1.45 (s, 3H), 1.39 (s, 3H), 1.38 (m, 2H); $^{13}$C NMR (75 MHZ, $CDCl_3$) δ137.3, 115.1, 110.4, 109.4, 80.3, 78.2, 73.3, 69.3, 68.2, 38.1, 34.9, 25.6, 25.5, 25.1, 24.0, 23.7; IR (neat) 3500 (m), 2936 (s), 2864 (m), 1450 (m), 1373 (m); MS (CI, $NH_3$) m/z (rel intensity) 316 [(M+$NH_4$)$^+$, 4], 299 [(M+H)$^+$, 24], 241 (29), 201 (100), 183 (59), 143 (41); HRMS (CI, $NH_3$) calcd for $C_{16}H_{26}O_5H$ [(M+H)$^+$] 299.1858, found 299.185; Anal. Calcd for $C_{16}H_{26}O_5$: C, 64.41; H, 8.78. Found C, 64.29; H, 8.68.

Methyl E-(6S,7S,8R)-6,7-Cyclohexylidenedioxy-8,9-isopropylidenedioxy-4-nonenoate (XV)

Trimethyl orthoacetate (75 mL, 625 mmol) and propionic acid (1.8 mL, 25 mmol) were added to a solution of the allylic alcohol 17 (36.5 g, 122 mmol) in toluene (500 mL). The flask was fitted with a distillation head and the mixture was heated at reflux, distilling off methanol as it formed. GC was used to monitor the disappearance of starting material ($t_R$=4.8 min) and the appearance of product ($t_R$=6.8 min, see General methods above for GC conditions). After 18 hours, the mixture was cooled to room temperature and concentrated to give 43 g (99%) of the title compound as a pale yellow oil that was used without further purification. Only one stereoisomer of (XV) was observed in the 300 MHz $^1$H NMR spectrum of the crude product. Purification of a small sample by chromatography (15:1 to 10:1 hex/EtOAc) provided an analytically pure sample, $R_f$=0.17 (8:1 hex/EtOAc); $[α]^{23}_D$–1.0 (c 1.71, $CHCl_3$); $^1$H NMR ($CDCl_3$, 360 MHz) δ5.83 (m, 1H), 5.57 (dd, J=7.1, 15.3 Hz, 1H), 4.63 (t, J=6.0 Hz, 1H), 4.04 (m, 3H), 3.93 (m, 1H), 3.68 (s, 3H), 2.41 (m, 4H), 1.5–1.7 (m, 8H), 1.40 (m, 2H), 1.39 (s, 3H), 1.32 (s, 3H); $^{13}$C NMR ($CDCl_3$, 90 MHz) δ173.3, 132.3, 126.7, 109.3, 109.2, 78.5, 77.6, 74.0, 67.3, 51.5, 37.6, 34.8, 33.4, 27.5, 26.7, 25.5, 25.1, 24.0, 23.7; IR (neat) 2986 (m), 2936 (s), 2862 (m), 1741 (s), 1440 (m) cm$^{-1}$; MS (El, 70 eV) m/z (rel intensity) 354 ($M^+$, 22), 155 (13), 101 (100); HRMS (El, 70 eV) calcd for $C_{19}H_{30}O_6$ ($M^+$) 354.2042, found 354.2028. Anal. Calcd for $C_{19}H_{30}O_6$: C, 64.39; H, 8.53. Found: C, 64.03; H, 8.50.

(5R)-5-[(1R,2S,3R,4R)-2,3-Cyclohexylidenedioxy-4,5-isopropylidenedioxy-1-hydroxypentyl] tetrahydrofuran-2-one (XVI) and (5S)-5-[(1S,2S,3R,4R)-2,3-Cyclohexyldenedioxy-4,5-isopropylidenedioxy-1-hydroxypentyl] tetrahydrofuran-2-one (XVII)

The dihydroxylation, was performed using the procedure reported by Sharpless. (Sharpless, K. B., et al. *J. Org. Chem.*, Vol. 57, pp. 2768–2771 (1992)). A solution of the crude alkene (XV) (43.0 a, 121 mmol) in tert-butanol (200 mL) was added to a cold (0° C.), mechanically stirred, biphasic mixture of water (500 mL) and tert-butanol (300 mL) containing potassium ferricyanide (120 g, 366 mmol), potassium carbonate (50 g, 366 mmol), potassium osmate dehydrate (0.225 g, 0.61 mmol), $(DHQD)_2$-PHAL (Sharpless, K. B., et al, *J. Org. Chem.*, Vol. 57, pp. 2768–2771 (1992)) (0.95 g, 1.2 mmol), and methanesulfonamide (12.8 g, 134 mmol). GC was used to monitor the disappearance of the alkene (XV) ($t_R$=6.8 min) and the appearance of the product ($t_R$=11.3 min, see General methods above for GC conditions). After 36 hours, sodium sulfite (185 g) was added and the mixture was stirred an additional 2 hours. EtOAc (500 mL) was then added, the layers were separated, and the aqueous layer was extracted with EtOAc (3×500 mL). The combined organic layers were washed with 2 M KOH (400 mL), then dried ($MgSO_4$) and concentrated. Crystallization, from hex/EtOAc (10:1) provided 26.8 g of lactone (XVI) in two crops. The mother liquor was concentrated to give a yellow oil that was purified by chromatography (4:1 to 2:1 hex/EtOAc gradient) to provide an additional 1.78 g of lactone (XVI) (combined yield 66% from 17) followed by 2.61 g (6%) of minor lactone diastereomer (XVII). Data for (XVI): $R_f$=0.15 (3:1 hex/EtOAc); $[α]^{23}_D$ –8.3 (c 1.38, $CHCl_3$); mp 139–141° C., $^1$H NMR ($CDCl_3$, 360 MHz) δ4.88 (m, 1H), 4.39 (dd, J=5.0, 9.6 Hz, 1H), 4.0–4.2 (m, 4H), 3.85 (dd, J=1.4, 3.7 Hz, lH), 3.80 (ddd, J=1.6, 3.7, 9.6 Hz. 1H), 2.74 (m, 1H), 2.46 (m, 1H), 2.35 (m, 2H), 1.5–1.7 (m, 8H), 1.43 (s, 3H), 1.39 (s, 3H), 1.37 (m, 2H); $^{13}$C NMR ($CDCl_3$, 90 MHz) δ177.9, 110.6, 109.7, 79.2, 77.7, 75.9, 73.2, 71.0, 68.0, 37.9, 34.6, 28.3, 26.5, 25.4, 24.9, 23.9, 23.8, 23.6; IR (neat) 3470 (br m), 2936 (s), 1776 (s), 1450 (w), 1372 (m) cm$^{-1}$; MS (El, 70 eV) m/z (rel intensity) 356 (M$^+$, 24), 313 (17), 255 (18), 101 (61), 85 (77), 55 (90), 43 (100); HRMS (El, 70 eV) calcd for C$_{18}$H$_{28}$O$_7$ (M$^+$) 356.1835, found 356.1836. Anal. Calcd for C$_{18}$H$_{28}$O$_7$; C, 60.66; H, 7.92. Found C, 60.74; H, 8.14. Data for (XVII): R$_f$=0.10 (3:1 hex/EtOAc); [α]$^{23}_D$+16.6 (c 1.34, CHCl$_3$), $^1$H NMR (CDCl$_3$, 360 MHz) δ4.78 (td, J=2.9, 6.9 Hz, 1H), 4.32 (t, J=5.8 Hz, 1H), 4.25 (dt, J=5.8, 9.6 Hz, 1H), 4.14 (dd, J=6.2, 8.8 Hz. 1H), 4.03 (m, 2H), 3.96 (dd, J=5.6, 8.7 Hz, 1H), 2.69 (dt, J=8.2, 17.5 Hz, 1H), 2.50 (m, 2H), 2.30 (m, 2H), 1.5–1.7 (m, 8H), 1.39 (m, 2H), 1.40 (s, 3H), 1.33 (s, 3H); $^{13}$C NMR (CDCl$_3$, 90 MHz) 177.6, 110.0, 109.6, 79.9, 77.6, 76.3, 73.3, 70.7, 68.2, 37.4, 34.5, 28.3, 26.8, 25.4, 25.0, 24.0, 23.6; IR (neat) 3465 (br, m), 2935 (s), 1776 (s), 1450 (w), 1370 (m) cm$^{-1}$; MS (EI, 70 eV) m/z (rel intensity) 356 (M$^+$, 66), 313 (58), 255 (48), 183 (65), 101 (96), 85 (100), 55 (86), 43 (92); HRMS (EI, 70 eV) calcd for C$_{18}$H$_{28}$O$_7$ (M$^+$) 356.1835, found 356.1831.

(5R)-5-[(1S,2S,3S,4R)-1-Azido-2,3-cyclohexylidenedioxy-4,5-isopropylidenedioxypentyl]tetrahydrofuran-2-one (XVIII)

Methanesulfonyl chloride (1.86 mL, 2.75 g, 24 mmol) was added to a cold (0° C.) solution of the alcohol (XVI) (7.13 g, 20.0 mmol) and 4-dimethylaminopyridine (0.120 g, 1.0 mmol) in pyridine (60 mL). The mixture was stirred for 10 min and then placed in a refrigerator (2° C.). After 24 hours, ether (300 mL) was added. and the solution was washed with 10% HCl (3×100 mL). The aqueous layers were back-extracted with ether (100 mL). The combined organic layers were washed with saturated NaHCO$_3$ and brine, then dried (MgSO$_4$), and concentrated to give 8.2 g of the crude mesylate as a foamy yellow solid that was used without further purification, R$_f$=0.22 (2:1 hex/EtOAc); $^1$H NMR (CDCl$_3$, 300 MHz) δ5.08 (m, 2H), 4.36 (dd, J=5.1, 6.7 Hz, 1H, 4.25 (dt, J=6.3, 9.4 Hz, 1H), 4.13 (dd, J=6.0, 8.6, 1 H), 4.07 (dd, J=5.1, 9.4 Hz, 1H), 3.91 (dd, J=6.5, 8.6 Hz, 1H), 3.20 (s, 3H), 2.75 (m, 1H), 2.53 (q, J=8.7 Hz, 1H), 2.41 (m, 2H), 1.58 (m, 8H), 1.41 (s,3H), 1.40 (m,2H), 1.36 (s, 3H); $^{13}$C NMR (CDCl$_3$, 75 MHz) δ176.1, 110.3, 109.4, 78.8, 78.0, 77.8, 75.4, 72.8, 68.3, 39.2, 37.6, 34.6, 27.8, 26.8, 25.5, 24.9, 23.9, 23.7. The crude mesylate was dissolved in THF (20 mL), tetra-n-butylammonium azide (Brändström, A., et al, *Acta Chem. Scand. B.,* Vol. 28, pp. 699–701 (1974)) (60 mL of a 1 M solution in THF, 60 mmol) was added, and the mixture was warmed to reflux. After 48 hours, the solution was cooled, poured into water (100 mL), and extracted with ether (3×200 mL). The combined organic extracts were washed with brine, then dried (MgSO$_4$), and concentrated. Chromatography (6:1 hex/EtOAc) provided 4.95 g (65%) of the title compound as a colorless oil, R$_f$=0.46 (2:1 hex/EtOAc); [α]$^{23}_D$–31.4 (c 0.90, CHCl$_3$); $^1$H NMR (CDCl$_3$, 300 MHz) δ4.80 (td, J=6.0, 7.2 Hz, 1H), 4.34 (m, 2H), 4.17 (dd, J=6.2, 8.7 Hz, 1H), 4.02 (dd, J=6.2, 9.6 Hz, 1H), 3.93 (m, 2H), 2.61 (m, 2H), 2.35 (m, 2H), 1.5–1.7 (m, 8H), 1.40 (s, 3H), 1.39 (m, 2H), 1.35 (s, 3H); $^{13}$C NMR (CDCl$_3$, 75 MHz) δ175.9, 110.1, 110.0, 78.9, 77.9, 75.9, 73.4, 68.5, 62.1, 36.9, 34.3, 28.3, 26.9, 25.4, 25.1, 24.2, 24.1, 23.8; IR (neat) 2936 (m), 2112 (s), 1784 (s), 1451 (w), 1372 (m) cm$^{-1}$; MS (El, 70 eV) m/z (rel intensity) 381 (M$^+$, 60), 338 (79), 183 (80), 101 (100), 85 (80); HRMS (EI, 70 eV) calcd for C$_{18}$H$_{27}$N$_3$O$_6$ (M$^+$) 381.1900, found 381.1903. Anal. Calcd for C$_{18}$H$_{27}$N$_3$O$_6$: C, 56.68; H, 7.13; N, 11.02. Found C, 56.58; H, 7.14; N, 10.89.

(5R)-5-[(1S,2S,3R,4R)-1-Azido-2,3-cyclohexylidenedioxy-4,5-dihydroxypentyl]tetrahydrofuran-2-one (XIX)

A solution of the azide (XVIII) (3.45 g, 9.05 mmol) in THF/isopropanol (1:1, 20 mL) was treated with 1 M sulfuric acid (10 mL). After 18 hours, the mixture was diluted with EtOAc (150 mL), washed with 20% Na$_2$CO$_3$ (50 mL) and brine (50 mL), then dried (MgSO$_4$), and concentrated. Chromatography (2:1 hex/EtOAc to 25:25:1 hex/EtOAc/EtOH gradient) provided 0.64 g, (19%) of recovered (XVIII) followed by 1.70 g (55%) of the title compound as a colorless oil, R$_f$=0.15 (50:50:1 hex/EtOAc/EtOH); [α]$^{23}_D$–21.8 (c 1.15, CHCl$_3$); $^1$H NMR (CDCl$_3$, 360 MHz) δ4.84 (q, J=6.8Hz, 1H), 4.36 (dd, J=4.6, 6.0 Hz, 1H), 4.08(dd, J=6.1, 9.6 Hz, 1H), 3.85–4.02 (m, 3H), 3.73 (m, 1H), 3.01 (m, 1H), 2.60 (m, 2H), 2.35 (m, 3H), 1.5–1.7 (m, 8H), 1.41 (m, 2H); $^{13}$C NMR (CDCl$_3$, 90 MHz) δ176.7, 109.9, 79.0, 76.0, 69.6, 64.7, 61.7, 36.7, 34,2, 28.2, 25.0, 24.1, 24.0, 23.7; IR (neat) 3390 (br, s), 2938 (s), 2862 (m), 2112 (s), 1775 (s) cm$^{-1}$; MS (CI, NH$_3$) m/z (rel intensity) 359 [(M+NH$_4$)$^+$, 64)], 342 [(M+H)$^+$, 18], 314 (100), 296 (47), 243 (69); HRMS (CI, NH$_4$) calcd for C$_{15}$H$_{23}$N$_3$O$_6$H [(M+H)$^+$] 342.1665, found 342.1673. Anal. Calcd for C$_{15}$H$_{23}$N$_3$O$_6$: C, 52.78; H, 6.79; N, 12.3 1. Found C, 52.79; H, 6.80; N, 12.14.

(5R)-5-[(1S,2S,3S,4R)-1-Azido-5-(tert-butyldimethylsilyloxy)-2,3-cyclohexylidenedioxy-4-methanesulfonyloxypentyl]tetrahydrofuran-2-one (XX)

tert-Butyldimethylsilyl chloride (0.77 g, 5.1 mmol) and imidazole (0.83 g, 12.2 mmol) were added to a cooled (0° C.) solution of the diol (XIX) (1.66 g, 4.86 mmol) in THF/DMF (2:1, 20 mL). After 1 hour, the mixture was poured into ether (100 mL) and washed with 1M HCl (2×50 mL). The combined aqueous layers were back-extracted with ether (2×50 mL). The combined organic layers were washed with saturated NaHCO$_3$ and brine, then dried (MgSO$_4$), filtered, and concentrated to give 2.25 g, of a pale yellow oil that was used without further purification, R$_f$=0.20 (4:1 hex/EtOAc); $^1$H NMR (CDCl$_3$, 360 MHz) δ4.83 (q, J=6.8 Hz, 1H), 4.34 (dd, J=4.0, 6.3 Hz, 1H), 4.06 (dd, J=6.4, 9.7 Hz, 1H), 3.98 (dd, J=4.0, 6.2 Hz, 1H), 3.91 (m, 1H), 3.86 (dd J=3.2, 9.8 Hz, 1H), 3.71 (dd, J=5.0, 9.9 Hz, 1H), 2.45–2.72 (m, 2H), 2.33 (m, 2H), 1.50–1.75 (m, 8H), 1.44 (m, 2H), 0.93 (s, 9H), 0.11 (s, 6H); $^{13}$C NMR (CDCl$_3$, 90 MHz) δ176.2, 109.8, 78.8, 75.9, 75.5, 69.2, 64.2, 61.8, 36.6, 34.2, 28.2, 25.8, 25.1, 24.2, 24.0, 23.7, 18.3, –5.4, –5.5. The crude alcohol was dissolved in pyridine (20 mL), 4-dimethylaminopyridine (30 mg, 0.24 mmol) was added, and the resulting, mixture was cooled to 0° C. Methanesulfonyl chloride (0.49 mL, 0.72 g, 6.3 mmol) was added in a dropwise fashion, and the mixture was stirred at 0° C. for 10 min, then placed in a refrigerator (2° C.). After 24 hours, ether (100 mL,) was added, and the solution was washed with 10% HCl (3×30 mL). The aqueous layers were back-extracted with ether (100 mL). The combined organic layers were washed with saturated NaHCO$_3$ (50 mL) and brine (30 mL), then dried (MgSO$_4$), and concentrated. Crystallization from ether/hexanes provided 1.96 g of the mesylate (XX). Concentration of the mother liquor followed by purification by chromatography (4:1 hex/EtOAc) provided another 0.23 g of (XX) (combined yield 84%), R$_f$=0.39 (2:1 hex/EtOAc); [α]$^{23}_D$–47.7 (c 1.20, CHCl$_3$); mp 109° C.; $^1$H NMR (CDCl$_3$, 360 MHz) δ5.02 (ddd, J=2.2, 3.6, 8.9 Hz, 1H), 4.76 (q, J=7.3 Hz, 1H), 4.52 (dd, J=2.3, 6.8 Hz, 1H), 4.42 (dd, J=6.9, 8.9 Hz, 1H), 4.18 (dd, J=2.2, 12.2 Hz, 1H), 3.94 (dd, J=3.7, 12.2 Hz, 1H), 3.69 (dd, J=2.2, 8.1 Hz, 1H), 3.12 (s, 3H), 2.4–2.7 (m, 3H), 2.30 (m, 1H), 1.75 (m, 2H), 1.3–1.7 (m, 6H), 1.41 (m, 2H), 0.92 (s, 9H), 0.11 (s, 6H); $^{13}$C NMR (CDCl$_3$, 90 MHz) δ176.9, 110.0, 80.3, 78.1, 75.1, 72.8, 62.1, 60.5, 39.6, 35.9, 33.6, 27.9, 25.8, 25.3. 25.0, 24.0, 23.6, 18.3, –5.5, –5.6; IR (neat) 2935 (s), 2858 (m), 2110 (s), 1788 (s) 1359

(s) cm$^{-1}$; MS (CI, NH$_3$) m/z (rel intensity) 551 [(M+NH$_4$)$^+$, 64], 410 (100), 352 (26), 243 (32); HRMS (CI, NH$_4$) calcd for C$_{22}$H$_{39}$N$_3$O$_8$SSiNH$_4$ [(M+NH$_4$)$^+$] 551.2571, found 551.2554. Anal. Calcd for C$_{22}$H$_{39}$N$_3$O$_8$SSi C, 49.5; H, 7.37; N, 7.87. Found C, 49.72; H, 7.25; N, 7.87.

(1S,2R,3S,8R,8aR)-3-[(tert-Butyldimethylsilyloxy) methyl]-1,2-cyclohexylidenedioxy-8-hydroxyindolizidin-5-one (XXI)

Palladium hydroxide on carbon (80 mg) was added to a solution of the azide XX (0.534 g, 1.0 mmol) in MeOH/EtOAc (1:1, 15 mL). The flask was evacuated by aspirator and purged with hydrogen three times, and the resulting heterogeneous mixture was stirred under a balloon of hydrogen. After 2 hours, the hydrogen was evacuated. and the mixture was filtered through Celite and concentrated. The residue was redissolve in MeOH (20 mL), and the solution was warmed to reflux. After 30 min, sodium methoxide (81 mg, 1.5 mmol) was added. The reaction was monitored by IR for the disappearance of the lactone carbonyl stretch at 1784 cm$^{-1}$ and the appearance of the lactam carbonyl stretch at 1630 cm$^-$. After 60 hours, the solution was cooled to room temperature and concentrated. The residue was dissolved in CH$_2$Cl$_2$/MeOH (10:1, 5 mL), florisil (200 mg) was added, and the mixture was stirred at room temperature for 30 min. The suspension was then filtered through Celite, and the filtrate was concentrated. Chromatography (50:1 to 10:1 CH$_2$Cl$_2$/MeOH gradient) provided 315 mg (77%) of the title compound as a colorless crystalline solid, R$_f$=0.20 (20:1 CH$_2$Cl$_2$/MeOH); mp 110° C.; [α]$^{23}_D$+38.7 (c 1.65, CHCl$_3$); $^1$H NMR (300 MHz, CDCl$_3$) δ4.85 (dd, J 4.9, 9.2 Hz, 1H), 4.71 (m, 2H), 4.13 (ddd, J=4.4, 8.8, 11.1 Hz, 1H), 3.95 (t, J=10.2 Hz, 1H), 3.52 (dt, J 4.3, 10.4 Hz, 1H), 3.21 (dd, J=4.9, 8.5 Hz, 1H), 2.65 (br s, 1H), 2.39 (m, 2H), 2.08 (m, 1H), 1.81 (m, 1H), 1.3–1.7 (m, 10H), 0.89 (s, 9H), 0.07 (s, 6H); $^{13}$C NMR (CDCl$_3$, 90 MHz) δ170.6, 112.1, 78.5, 76.7, 67.5, 65.7, 64.7, 59.2, 35.9, 34.4, 31.0, 29.2, 25.8, 25.1, 23.9, 23.6, 18.3, −5.4, −5.5; IR (neat) 3380 (br m), 2935 (s), 2856 (m), 1633 (s) 1101 (s) cm$^{-1}$; MS (CI, NH$_3$) m/z (rel intensity) 412 [(M+H)$^+$, 100], 354 (8); HRMS calcd for C$_{21}$H$_{37}$NO$_5$SiH [(M+H)$^+$] 412.2519, found 412.2519. Anal. Calcd for C$_{21}$H$_{37}$NO$_5$Si: C, 61.28; H, 9.06; N, 3.40. Found C, 60.98; H, 9.16; N, 3.43.

(1S,2R,3S,8R,8aR)-3-[(tert-Butyldimethylsilyloxy) methyl]-1,2-cyclohexylidene-8-hydroxyindolizidine (XXII)

Borane-methyl sulfide complex (1.0 mL of a 2 M solution in THF, 2.0 mmol) was added to a cooled (0° C.) solution of the lactam (XXI) (206 mg, 0.50 mmol) in THF (10 mL). After 15 min, the solution was allowed to warm to room temperature. After 4 hours, the reaction was quenched by the slow addition of ethanol (8 mL) and then concentrated. The residue was redissolved in EtOH (10 mL), and the solution was warmed to reflux. After 2 hours, the mixture was cooled to room temperature and concentrated. Chromatography (4:1 hex/EtOAc) provided 188 mg (94%) of the title compound as a colorless crystalline solid, R$_f$=0.19 (4:1 hex/EtOAc); mp 108° C.; [α]$^{23}_D$+22.0 (c 1.70, CHCl$_3$); $^1$H NMR (300 MHz, CDCl$_3$) δ4.68 (dd, J=4.6, 6.4 Hz, 1H), 4.60 (dd, J=4.3, 6.3 Hz, 1H), 3.92 (dd, J=6.9, 9.9 Hz, 1H), 3.81 (m, 1H), 3.74 (dd, J=5.2, 9.9 Hz, 1H), 3.11 (m, 1H), 2.23 (m, 2H), 2.05 (m, 1H), 1.4–1.9 (m, 13H), 1.25 (m, 2H), 0.90 (s, 9H), 0.08 (s, 3H), 0.07 (s, 3H); $^{13}$C NMR (CDCl$_3$, 90 MHz) δ112.2, 79.2, 77.7, 74.7, 70.5, 67.6, 61.3, 51.2, 35.8, 35.5, 33.2, 26.0, 25.4, 24.3, 24.2, 24.0, 18.4, −5.2: IR (neat) 3305 (br, m), 2929 (s), 2856 (m), 2800 (w) cm$^-$; MS (CI, NH$_3$) m/z (rel intensity) 398 [(M+H)$^+$, 47],382 (20), 340 (14), 252 (100); HRMS calcd for C$_{21}$H$_{39}$NO$_4$SiH [(M+H)$^+$] 398.2727, found 398.2730. Anal. Calcd for C$_{21}$H$_{39}$NO$_4$Si: C, 63.43; H, 9.89; N, 3.52. Found C, 63.51; H, 9.86; N, 3.64.

(1S,2R,3S,8R,8aR)-3-(Hydroxymethyl)-1,2,8-trihydroxyindolizidine[(3S)-3-(Hydroxymethyl) swainsonine] (VIII)

A solution of the indolizidine (XXII) (140 mg, 0.35 mmol) in THF (3.5 mL) was treated with 6N HCl (3.5 mL) at room temperature. After 24 hours, the solution was concentrated, and the residue was redissolved in MeOH (5 mL). Dowex 1×8 200 mesh OH$^-$ ion exchange resin (2 g) was added, and the mixture was stirred for 15 min. The mixture was then filtered, and the filtrate concentrated. Chromatography (100:25:1 CH$_2$Cl$_2$/MeOH/Aq. NH$_4$OH gradient) provided 57 mg (80%) of the title compound as a colorless oil, R$_f$=0.57 (50:25:1 CH$_2$Cl$_2$/MeOH/Aq. NH$_4$OH); [α]$^{23}_D$ −27.0 (c 0.50, MeOH); $^1$H NMR (300 MHz, CD$_3$OD) δ4.25 (dd, J=5.5, 8.3 Hz, 1H, H$_2$), 4.11 (dd, J=3.3, 5.5 Hz, 1H, H$_1$), 3.74 (m, 2H, H8 and H$_9$), 3.61 (dd, J=3.4, 11.3 Hz, 1H, H$_9$), 3.05 (m, 1H, H$_{5eq}$), 2.52 (m, 1H, H$_3$), 2.25 (m, 1H, H$_{7eq}$), 1.95 (td, J=3.2, 11.2 Hz, 1H, H$_{5ax}$) 1.88 (dd, J=3.2, 9.1 Hz, 1H, H$_{8a}$), 1.5–1.7 (m, 2H, H$_{6eq}$ and H$_{6ax}$), 1.21 (qd, J=5.0, 12.5 Hz, 1H, H$_{7ax}$); $^{13}$C NMR (CD$_3$OD, 90 MHz) δ73.5, 72.4, 70.5, 69.0, 67.2, 60.3, 52.1, 34.7, 25.0: IR (neat) 3350 (br s), 2938 (m), 2800 (w), 1142 (m), 1083 (m) cm$^{-1}$, MS (CI, NH$_3$) m/z (rel intensity) 204 [(M+H)$^+$, 100], 150 (28), 136 (34); HRMS calcd for C$_9$H$_{17}$NO$_4$H [(M+H)$^+$] 204.1236, found 204.1226.

(5R)-5-[(1S,2S,3R,4S)-1-Azido-2,3-cyclohexylidenedioxy-4,5-epoxypentyl] tetrahydrofuran-2-one (XXIII)

In a glove bag under an atmosphere of dry N$_2$, anhydrous cesium fluoride (0.305 g, 2.0 mmol) was transferred to a flask containing a magnetic stir bar. A rubber septum was placed on the flask before removing from the glove bag. The cesium fluoride was then suspended in CH$_3$CN (15 mL) and the mesylate (XX) (534 mg, 1.0 mmol) was added as a solution in CH$_3$CN (5 mL). The flask was then fitted with a condenser, and the mixture was warmed to reflux. After 2 hours, the mixture was cooled to room temperature, then poured into EtOAc (100 mL) and washed with water (30 mL) and brine (30 mL). The aqueous layers were back-extracted with EtOAc (50 mL). The combined organic layers were dried (Na$_2$SO$_4$), then filtered and concentrated. Chromatography (2:1 hex/EtOAc) provided 0.310 g, (96%) of the title compound as a colorless oil, R$_f$=0.13 (2:1 hex/EtOAc); [α]$^{23}_D$ −22.0 (c 0.60, CHCl$_3$); $^1$H NMR (CDCl$_3$, 300 MHz) δ4.66 (q, J=7.4 Hz, 1H), 4.44 (dd, J=4.1, 7.0 Hz, 1H), 3.95 (dd, J=6.1, 6.9 Hz, 1H), 3.45 (dd, J=4.1, 7.7 Hz, 1H), 3.26 (ddd, J=2.7, 4.1, 6.0 Hz, 1H), 2.84 (dd, J=4.2, 4.9 Hz, 1H), 2.64 (m, 3H), 2.50 (m, 1H), 2.26 (m, 1H), 1.3–1.9 (m, 10H); $^{13}$C NMR (CDCl$_3$, 90 MHz) δ175.7, 110.7, 78.2, 78.0, 76.3, 62.6, 50.5, 43.4, 35.9, 34.0, 28.0, 25.2, 25.0, 24.0, 23.7; IR (neat) 2936 (s), 2860 (m), 2113 (s), 1784 (s) cm$^{-1}$; MS (EI, 70 eV) m/z (rel intensity) 323 (M$^+$, 40), 294 (25), 280 (100), 183 (28), 85 (53), 55 (70); HRMS (EI, 70 eV) calcd for C$_{15}$H$_{21}$N$_3$O$_5$ (M$^+$) 323.1481, found 323.1483.

(1S,2R,3R,8R,8aR)-1,2-Cyclohexylidenedioxy-3-(hydroxymethyl)-8-hydroxyindolizidin-5-one (XXIV)

Palladium hydroxide on carbon (70 mg) was added to a solution of the azide XXIII (0.460 g, 1.42 mmol) in MeOH/

EtOAc (1:1, 22 mL). The flask was evacuated by aspirator and purged with hydrogen three times, and the resulting heterogeneous mixture was stirred under a balloon of hydrogen. After 2 hours, the hydrogen was evacuated, and the mixture was filtered through Celite and concentrated. The residue was redissolved in MeOH (25 mL), sodium methoxide (80 mg, 1.48 mmol) was added, and the solution was warmed to reflux. The reaction was monitored by IR for the disappearance of the lactone carbonyl stretch at 1784 cm$^{-1}$ and the appearance of the lactam carbonyl stretch at 1615 cm$^{-1}$. After 60 hours, the solution was cooled to room temperature and concentrated. The mixture was diluted with $CH_2Cl_2$/MeOH (10:1, 5 mL), florisil (200 mg) was added, and the mixture was stirred at room temperature for 30 min. The suspension was then filtered through Celite, and the filtrate was concentrated. Chromatography (20:1 $CH_2Cl_2$/MeOH) provided 270 mg (64%) of the title compound as a colorless crystalline solid, $R_f$=0.34 (10:1 $CH_2Cl_2$/MeOH); mp 190° C.; $[\alpha]^{23}_D$ −32.7 (c 0.55, MeOH); $^1$H NMR (300 MHz, $CDCl_3$) δ4.83 (t, J=5.3 Hz, 1H), 4.60 (d, J=5.9 Hz, 1H), 4.43 (br t, J=5.0 Hz, 1H), 4.10 (ddd, J=4.0, 8.6, 11.4 Hz, 1H), 3.85 (dd, J=4.1, 10.9 Hz, 1H), 3.69 (dd, J=6.4, 11.0 Hz, 1H), 3.65 (dd, J=4.8, 8.6 Hz, 1H), 2.35–2.60 (m, 3H), 2.11 (m, 1H), 1.89 (qd, J=6.8, 11.6 Hz, 1H), 1.3–1.7 (m, 1H); $^{13}$C NMR ($CDCl_3$, 90 MHz) δ169.8, 113.1, 80.0, 79.4, 66.3, 65.9, 65.3, 63.3, 36.3, 34.4, 29.7, 29.1, 25.0, 24.0, 23.7; IR (neat) 3360 (br m), 2930 (m), 2860 (m), 1614 (s) cm$^{-1}$; MS (EI, 70 eV) m/z (rel intensity) 297 (M$^+$, 73), 266 (71), 254 (100), 152 (46), 134 (70), 85 (44); HRMS, calcd for $C_{15}H_{23}NO_5$ (M$^+$) 297.1576, found 297.1589. Anal. Calcd for $C_{15}H_{23}NO_5$: C, 60.59; H, 7.80; N, 4.71. Found C, 60.44; H, 7.75; N, 4.48.

(1S,2R,3R,8R,8aR)-1,2-Cyclohexylidenedioxy-3-(hydroxymethyl)-8-hydroxyindolizidine (XXV)

Borane-methyl sulfide complex (1.25 mL of a 2 M solution in THF, 2.5 mmol) was added to a cooled (0° C.) solution of the lactam (XXIV) (140 mg, 0.47 mmol) in $CH_2Cl_2$ (10 mL). The solution was allowed to warm to room temperature. After 4 hours, the reaction was quenched by the slow addition of ethanol (8 mL) and then concentrated. The residue was redissolved in EtOH (10 mL), and the solution was warmed to reflux. After 2 hours, the mixture was cooled to room temperature and concentrated. Chromatography (50:1 to 10:1 $CH_2Cl_2$/MeOH gradient) provided 132 mg (99%) of the title compound as a colorless crystalline solid, $R_f$ 0.21 (20:1 $CHCl_3$/MeOH); mp 172° C.; $[\alpha]^{23}_D$ −75.1 (c 1.40, MeOH); $^1$H NMR (300 MHz, $CDCl_3$) δ4.75 (t, J=6.5 Hz, 1H, $H_1$), 4.70 (dd, J=2.2, 7.0 Hz, 1H, $H_2$), 3.75 (m, 1H, $H_8$), 3.68 (m, 2H, $H_9$), 3.25 (dd, J=2.7, 5.3 Hz, 1H, $H_3$), 2.87 (m, 3H, $H_{8a}$, $H_5$ and $H_{OH}$), 2.57 (td, J=3.3, 12.6 Hz, 1H, $H_5$), 2.25 (br s, 1H, $H_{OH}$), 2.07 (m, 1H, $H_7$), 1.78 (m, 2H), 1.5–1.7 (m, 8H), 1.41 (m, 2H), 1.34 (m, 1H, $H_7$); $^{13}$C NMR ($CDCl_3$, 90 MHz) δ113.7, 81.7, 79.2, 68.7, 66.6, 65.2, 59.5, 44.8, 35.4, 33.8, 32.0, 25.1, 24.1, 23.5, 21.0; IR (neat) 3375 (br m), 2930 (s), 2860 (m), 1441 (m) cm$^{-1}$; MS (CI, $NH_3$) m/z (rel intensity) 284 [(M+H)$^+$, 100], 252 (69); HRMS calcd for $C_{15}H_{25}NO_4H$ [(M+H)$^+$] 284.1861, found 284.1864. Anal. Calcd for $C_{15}H_{25}NO_4$: C, 63.58; H, 8.89; N, 4.94. Found C, 63.76; H, 8.93; N, 4.88.

(1S,2R,3R,8R,8aR)-3-(Hydroxymethyl)-1,2,8-trihydroxyindolizidine [(3R)-3-(Hydroxymethyl) swainsonine] (VII)

A solution of the indolizidine XXV (110 mg, 0.39 mmol) in THF (4 mL) was treated with 6N HCl (4 mL) at room temperature. After 24 hours, the solution was concentrated, and the residue was redissolved in MeOH (5 mL). Dowex 1×8 200 mesh OH$^-$ ion exchange resin (2 g) was added, and the mixture was stirred for 15 min. The mixture was then filtered, and the filtrate was concentrated. Chromatography (75:25:1 to 50:25:1 $CH_2Cl_2$/MeOH/Aq. $NH_4OH$ gradient) provided 59 mg (75%) of the title compound as a colorless oil, $R_f$=0.26 (50:25:1 $CH_2Cl_2$/MeOH/Aq. $NH_4OH$); $[\alpha]^{23}_D$ −47.9 (c 0.78, MeOH); $^1$H NMR (360 MHz, $CD_3OD$) δ4.14 (dd, J=3.8, 5.6 Hz, 1H, $H_1$), 4.08 (dd, J=4.4, 5.6 Hz, 1H, $H_2$), 3.78 (ddd, J=4.6, 9.2, 11.3 Hz, 1H, $H_8$), 3.71 (dd, J=4.1, 11.6 Hz, 1H, $H_9$), 3.68 (dd, J=4.2, 11.6 Hz, 1H, $H_9$), 2.98 (dd, J=4.2, 8.4 Hz, 1H, $H_3$), 2.94 (m, 1H, $H_{5eq}$), 2.57 (dd, J=4.0, 9.4 Hz, 1H, $H_{8a}$) 2.54 (dd, J=4.5, 11.8 Hz 1H, $H_{5ax}$), 1.99 (m, 1H, $H_{7eq}$), 1.50–1.65 (m, 2H, $H_6$), 1.20 (qd, J=5.4, 12.0 Hz, 1H, $H_{7ax}$); $^{13}$C NMR ($CD_3OD$, 90 MHz) δ74.3, 71.8, 71.3, 69.5, 67.6, 61.9, 46.8, 34.1, 23.9; IR (neat) 3355 (br s), 2935 (m), 2860 (w), 1444 (w), 1071 (m) cm$^{-1}$; MS (CI, $NH_3$) m/z (rel intensity) 204 [(M+H)$^+$, 100], 168 (48), 150 (75), 136 (56); HRMS calcd for $C_9H_{17}NO_4H$ [(M+H)$^+$] 204.1236, found 204.1236.

Obviously, numerous modifications and variations of the present invention are possible in light of the above teachings. It is therefore to be understood than, within the scope of the appended claims, the invention may be practiced otherwise than as specifically described herein.

What is claimed as new and desired to be secured by Letters Patent of the United States is:

1. A compound having the formula (II)

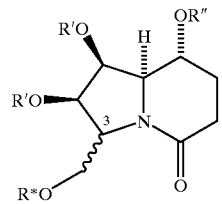

wherein:
each $R^1$, independently of the other, is H, acetyl, benzyl, methoxymethyl, tosyl, mesyl, trifluoromesyl, $tri(C_{1-4}$ alkyl)silyl, di($C_{1-4}$ alkyl)phenylsilyl, diphenyl($C_{1-4}$ alkyl)silyl, triphenylsilyl, or together both R' form a $C_{3-6}$ alkylidene protecting group;
each R", independently of the other, is H, acetyl, benzyl, methoxymethyl, tosyl, mesyl, trifluoromesyl, tri($C_{1-4}$ alkyl)silyl, di($C_{1-4}$ alkyl)phenylsilyl, diphenyl($C_{1-4}$ alkyl)silyl, or triphenylsilyl; and
R* is
H;
straight chain $C_{1-22}$-alkyl;
branched $C_{3-22}$-alkyl;
$C_{3-8}$-cycloalkyl;
$C_{3-8}$-cycloalkyl substituted with straight chain $C_{1-22}$-alkyl;
$C_{3-8}$-cycloalkyl substituted with branched $C_{3-22}$-alkyl;
a group of the formula

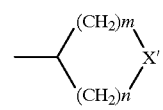

wherein:
X'=O, S, NH, $NR^1$ ($R^1$ is $C_{1-22}$-alkyl), or NAr, m=0–5;
n=0–5; and
m+n≧2;
—(CH₂)ₙ'Ar (n'=1 to 22);
—(CH₂)ₙ'G (n'=1 to 22);
—Ar; and
—G;
wherein Ar is:

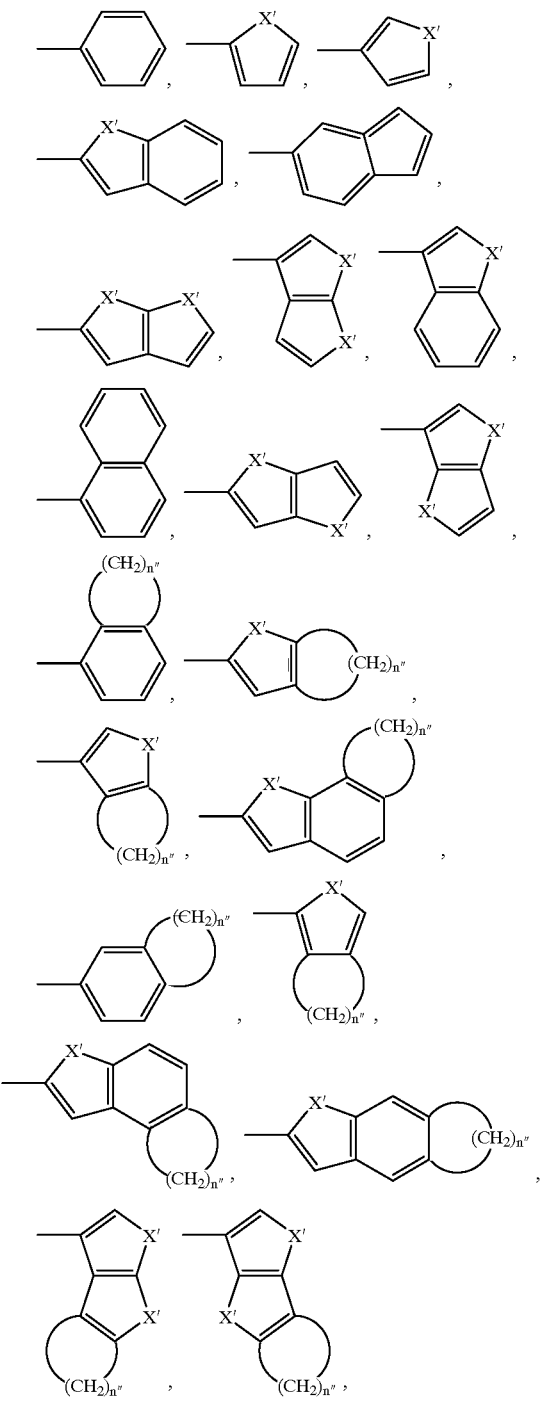

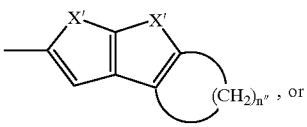

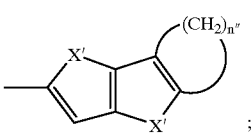

where
n"=2 to 5;
X'=NH, NR¹ (R¹ is $C_{1-22}$-alkyl), NAr, O, or S
and each carbon atom may be substituted with halogen, $C_{1-22}$-alkyl, $C_{6-10}$-aryl or G;
wherein G is:
F, Cl, Br, I,
—CN, —CHO, —COR¹, —CHNOH, —CHNOR¹, —CR¹NOH, —CR¹NHOR², —CN, —CO₂H, —CO₂R¹, —CONH₂, —CONHR¹, —CONR¹R², —CSNH₂, —CSNHR¹, —CSNR¹R², —C(NH)OR¹, —C(NR)OR¹, —C(NH)SR¹, —C(NR)SR¹, —C(NH)NH₂, —C(NR¹)NH₂, —C(NH)NR¹R², —C(NR)R¹R², —C(NR¹)NHR², —CONHOH, —CONR¹OH, —CONHOR¹, —CONR¹OR², —CONHNH₂, —CONR¹NH₂, —CONHNR¹R², —CONR¹NHR², -or CONR¹NR²R³, (wherein R¹, R², and R³ are each independently $C_{1-22}$-alkyl).

2. The compound of claim 1, wherein both R' together form a $C_{3-6}$ alkylidene protecting group.

3. The compound of claim 1, wherein both R' together form a cyclohexylidene protecting group.

4. The compound of claim 1, wherein R" is H.

5. The compound of claim 1, wherein R* is H.

6. The compound of claim 1, wherein both R' together form a $C_{3-6}$ alkylidene protecting group and R" is H.

7. The compound of claim 1, wherein both R' together form a $C_{3-6}$ alkylidene protecting group and R* is H.

8. The compound of claim 1, wherein both R' together form a $C_{3-6}$ alkylidene protecting group, R" is H, and R* is H.

9. The compound of claim 1, wherein both R' together form a cyclohexylidene protecting group and R" is H.

10. The compound of claim 1, wherein both R' together form a cyclohexylidene protecting group and R* is H.

11. The compound of claim 1, wherein both R' together form a cyclohexylidene protecting group group, R" is H, and R* is H.

* * * * *

UNITED STATES PATENT AND TRADEMARK OFFICE
CERTIFICATE OF CORRECTION

PATENT NO.     : 6,262,065 B1
DATED          : July 17, 2001
INVENTOR(S)    : William H. Pearson et al.

It is certified that error appears in the above-identified patent and that said Letters Patent is hereby corrected as shown below:

Column 1,
Line 45, "Rahmaii" should read -- Rahman --.

Column 2,
Line 12, "25143" should read -- 2143 --.
Line 31, "1604" should read -- 1364 --.
Line 45, "*Sylett*" should read -- *Synlett* --.

Column 3,
Line 5, "inventors" should read -- inventors' --.

Column 4,
Line 61, "-NH(C=O)NR$^1$R$^1$" should read -- NH(C=O)NR$^1$R$^2$ --.

Column 5,
Line 9, "-(NH)NH$_2$" should read -- C(NH)NH$_2$ --.
Line 12, "-CONHNR$^1$R$^1$" should read -- -CONHNR$^1$R$^2$ --.
Line 16, "R$^1$" should read -- R´ --.

Column 14,
Line 36, "198" should read -- 1198 --.
Line 47, "Vol." should read -- Vol. 3, --.
Line 60, "Ralmuan" should read -- Rahman --.

Column 24,
Line 57, "R$_r$" should read -- R$_f$ --.

Column 25,
Line 4, "49.5" should read -- 49.51 --.
Line 23, "1630 cm" should read -- 1630 cm$^{-1}$ --.

UNITED STATES PATENT AND TRADEMARK OFFICE
CERTIFICATE OF CORRECTION

PATENT NO. : 6,262,065 B1
DATED : July 17, 2001
INVENTOR(S) : William H. Pearson et al.

It is certified that error appears in the above-identified patent and that said Letters Patent is hereby corrected as shown below:

<u>Column 26,</u>
Line 1, "cm" should read -- $cm^{-1}$ --.

Signed and Sealed this

Fifth Day of March, 2002

*Attest:*

JAMES E. ROGAN
*Attesting Officer*     *Director of the United States Patent and Trademark Office*